US011894160B2

(12) United States Patent
Kozioziemski

(10) Patent No.: US 11,894,160 B2
(45) Date of Patent: Feb. 6, 2024

(54) LIGHT FIELD X-RAY OPTICS

(71) Applicant: Lawrence Livermore National Security, LLC, Livermore, CA (US)

(72) Inventor: Bernard J. Kozioziemski, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 65 days.

(21) Appl. No.: 17/613,477

(22) PCT Filed: May 23, 2019

(86) PCT No.: PCT/US2019/033743
§ 371 (c)(1),
(2) Date: Nov. 22, 2021

(87) PCT Pub. No.: WO2020/236181
PCT Pub. Date: Nov. 26, 2020

(65) Prior Publication Data
US 2022/0223311 A1    Jul. 14, 2022

(51) Int. Cl.
*G01N 23/04* (2018.01)
*G21K 1/06* (2006.01)
*G21K 7/00* (2006.01)

(52) U.S. Cl.
CPC ............ *G21K 1/065* (2013.01); *G01N 23/04* (2013.01); *G21K 1/062* (2013.01); *G21K 7/00* (2013.01); *G21K 2201/067* (2013.01)

(58) Field of Classification Search
CPC .......... G21K 1/06; G21K 1/065; G21K 1/062; G21K 7/00; G21K 2201/067; G01N 23/04; A61B 6/03; A61B 6/4291
See application file for complete search history.

(56) References Cited

U.S. PATENT DOCUMENTS 6,124,974 A    9/2000  Burger
8,290,358 B1  10/2012  Georgiev

FOREIGN PATENT DOCUMENTS

EP    2623964    *  8/2013
EP    2623964 A1    8/2013

OTHER PUBLICATIONS

Bajt, Saša et al., "X-ray focusing with efficient high-NA multilayer Laue lenses," Light: Science & Applications (2018) 7, 17162; doi:10.1038/lsa.2017.162, 9 pages.
(Continued)

*Primary Examiner* — Jurie Yun
(74) *Attorney, Agent, or Firm* — Perkins Coie LLP

(57) ABSTRACT

Devices, systems and methods for performing X-ray scans with a single line of sight using a lens array for capturing the light field of the X-rays are described. In one example aspect, an X-ray optical system includes a primary optics subsection positioned to receive incoming X-rays after traversal through an object and to redirect the received incoming X-rays onto an intermediate image plane. The system also includes a microlens array positioned at or close to the intermediate image plane to receive at least some of the received incoming X-rays after redirection by the primary optics subsection to diffract the X-rays that are incident thereupon.

15 Claims, 24 Drawing Sheets

(56) References Cited

OTHER PUBLICATIONS

Dos Santosa Rolo, Tommy, et al. "A Shack-Hartmann Sensor for Single-Shot Multi-Contrast Imaging with Hard X-rays," Appl. Sci. 2018, 8, 737; doi:10.3390, Published May 7, 2018, 13 pages.
International Search Report and Written Opinion received in Application No. PCT/US19/33743, dated Aug. 8, 2019, 9 pages.
Mikhaylov, Andrey, et al., "Shack-Hartmann wavefront sensors based on 2D refractive lens arrays and super-resolution multi-contrast X-ray imaging," J. Synchrotron Rad. (2020). 27, 788-795.

* cited by examiner

LIGHT FIELD X-RAY OPTICS

STATEMENT REGARDING FEDERALLY SPONSORED RESEARCH

The United States Government has rights in this invention pursuant to Contract No. DE-AC52-07NA27344 between the U.S. Department of Energy and Lawrence Livermore National Security, LLC, for the operation of Lawrence Livermore National Laboratory.

CROSS REFERENCE TO RELATED APPLICATIONS

This application is a 371 National Phase Application of International Patent Application No. PCT/US2019/033743, filed on May 23, 2019. All the contents of the aforementioned patent application are hereby incorporated by reference in their entireties.

TECHNICAL FIELD

This document relates to optical systems for tomographic imaging, an in particular to X-ray tomographic systems.

BACKGROUND

Tomography is imaging through the use of penetrating waves. In many cases, images are obtained based on the tomographic reconstruction. To obtain a better understanding of a target structure, multiple scans of the structure from different views are usually required. For example, X-ray computed tomography can be produced from multiple radiographs.

SUMMARY

Disclosed are devices, systems and methods for determining three-dimensional structures of a target object by performing X-ray scans. In some embodiments, the disclosed devices and systems use a single line of sight and rely on a lens array capable of capturing the light field of the X-rays.

In one example aspect, an X-ray optical system is disclosed. The X-ray optical system includes a primary optics subsection positioned to receive incoming X-rays after traversal through an object and to redirect the received incoming X-rays onto an intermediate image plane. The X-ray optical system also includes a microlens array positioned at or close to the intermediate image plane to receive at least some of the received incoming X-rays after redirection by the primary optics subsection to diffract the X-rays that are incident thereupon.

In another example aspect, a lens array for use in a light field X-ray microscopy system is disclosed. The lens array includes a first set of multilayer Laue lenses (MLLs) positioned side-by-side in first plane, each MLL in the first set including a set of layers arranged in a first direction. The lens array also includes a second set of MLLs positioned side-by-side in a second first plane, each MLL in the second set including a set of layers arranged in a second direction. The first and the second plane are selected to allow the first set of MLLs to receive an incoming X-ray beam and to redirect the incoming X-ray beam, and the second set of MLLs to receive the redirected X-ray beam onto a focal plane of the lens array. Numbers and thicknesses of the set of layers in the first set of MLLs and in the second set of MLLs are selected to produce a predetermined focal length for the lens array for a given energy level of the incoming X-ray beam.

The above and other aspects and their implementations are described in greater detail in the drawings, the descriptions, and the claims.

DETAILED DESCRIPTION

Three-dimensional imaging, such as tomographic scans for X-ray medical imaging, is routinely used to acquire details about the internal structure of items including humans. These tomographic scans require acquiring multiple views in sequence in order to probe the internal structure. Any motions during the acquisition process can introduce motion blurring, which may greatly deteriorate image quality and lead to reduced resolution in dynamic imaging of the target structure. Additionally, the ability to rotate an imaging system around a target item to obtain multiple views can limit the size of the system and the type of target items to scan.

Limited angle tomography is an attempt to reduce the number of views needed to produce a three-dimensional (3D) image. However, limited angle tomography does not eliminate the need for multiple-view scanning. Predictive algorithms encompassing a variety of statistical techniques from data mining, predictive modelling, and machine learning can be used to reduce motion blurring in dynamic imaging, but such algorithms require a good understanding of the geometry to accurately reduce or remove the motion blurring.

This patent document describes techniques that can be implemented in various X-ray imaging systems that among other features and benefits allow sampling the internal structure of a target item with high resolution using a single line of sight without rotating or moving the target item. The disclosed techniques reduce the need for bulky equipment and can enable small regions within large items to be sampled. Scanning using a single line of sight also allows implementation of short measurement processes, such as dynamic experiments in the High Energy Density (HED) regime in which repeated measurements cannot be made.

X-rays have much higher frequency and photon energy, thus the interaction between X-rays and matter is very different from visible light. Visible light is easily redirected using lenses and mirrors, but X-rays tend to penetrate in most materials without changing directions because the refractive index of most materials is close to 1 for X-rays. The most common technique that is used to direct X-rays is reflection at grazing incidence angles, either using total external reflection at very small angles or multilayer coatings. Other techniques used for manipulating X-rays include diffraction and interference in the form of zone plates, refraction in compound refractive lenses, Bragg reflection from a crystal plane in flat or bent crystals.

Figure 1A:
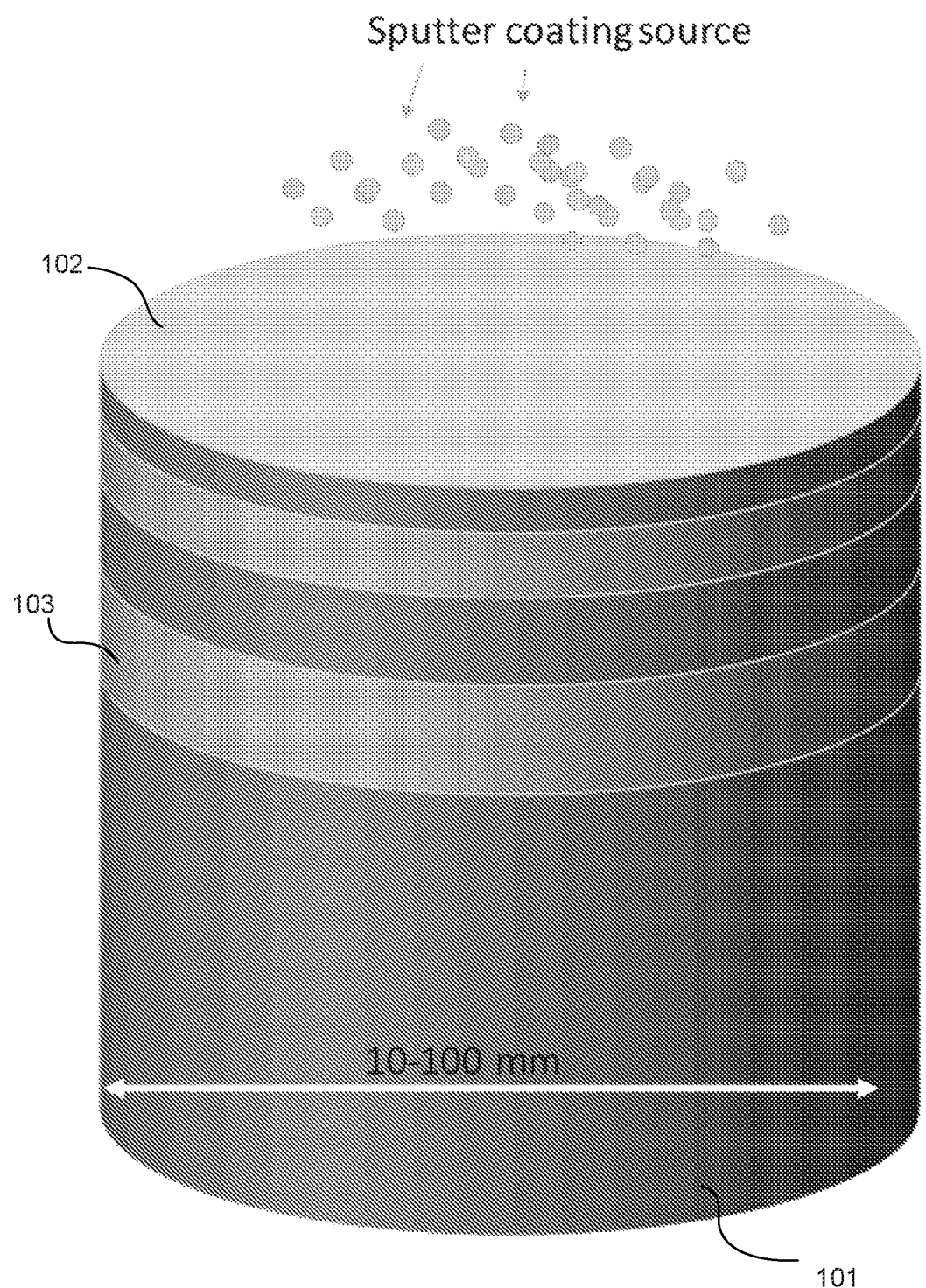
FIG. 1A illustrates an example coating process for creating a one-dimensional (1D) multilayer Laue Lens (MLL).
Figure 1B:
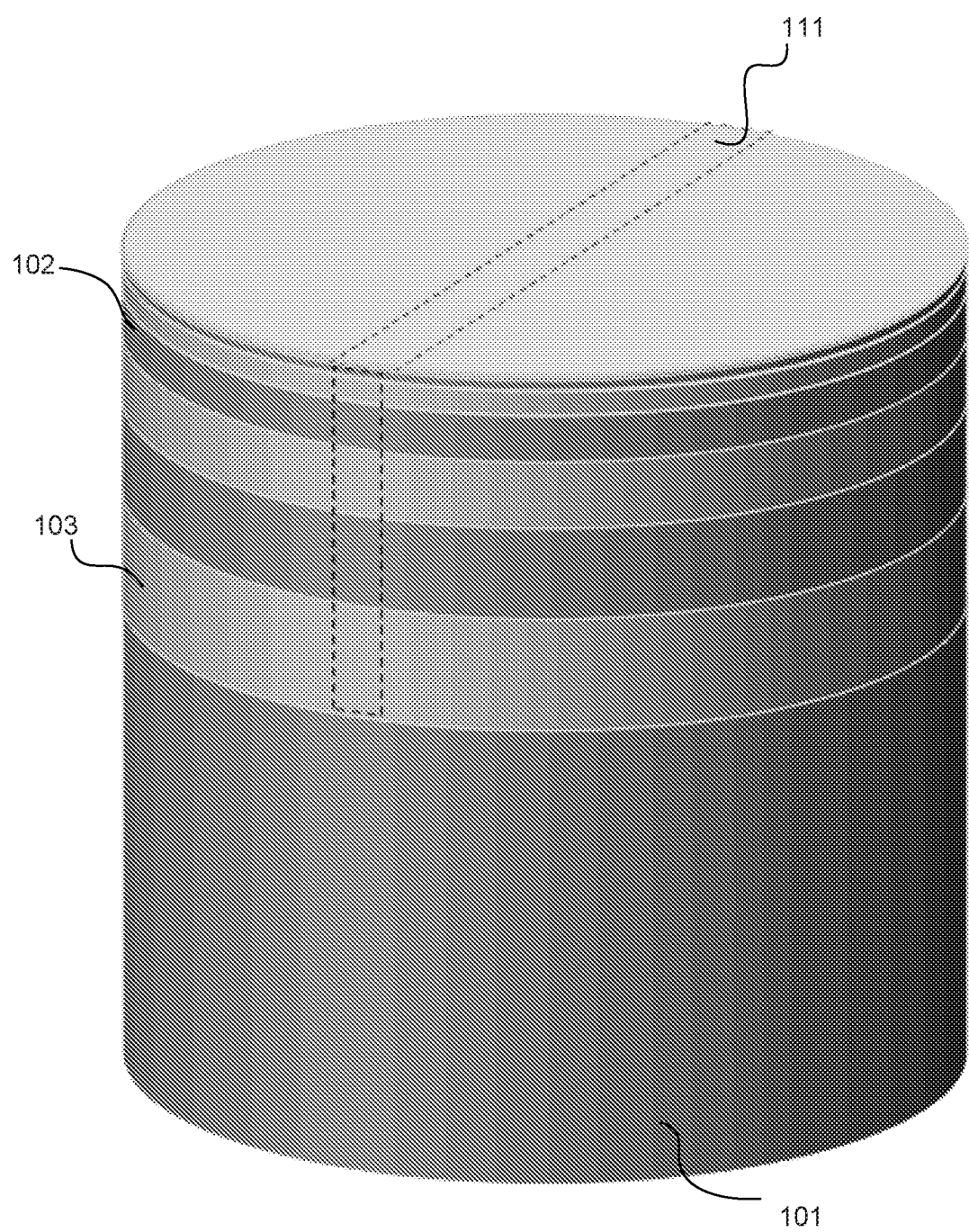
FIG. 1B illustrates an example slice to be extracted to form a 1D MLL.
Figure 1C:
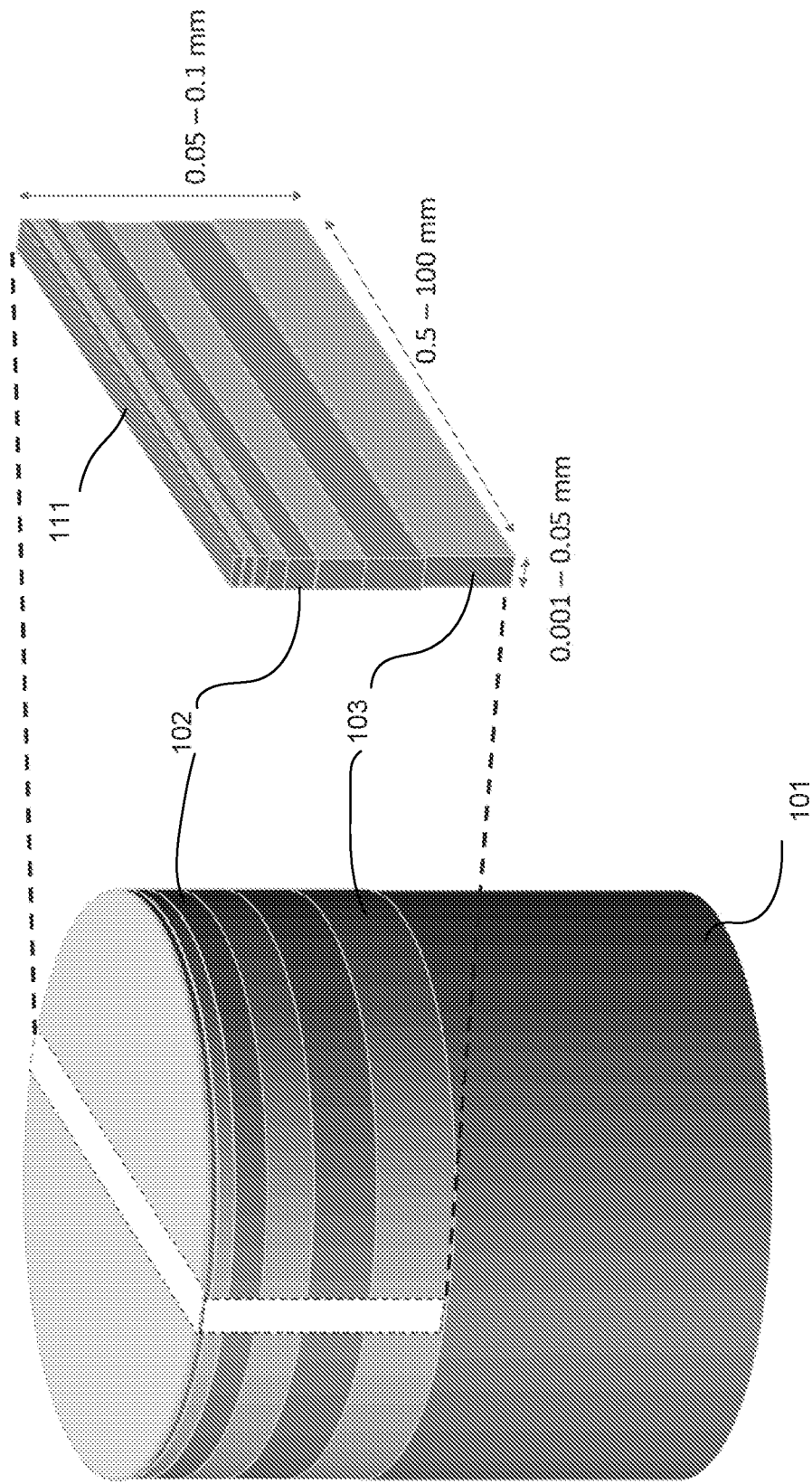
FIG. 1C illustrates a schematic diagram of an extracted slice to form a 1D MLL.

The Multilayer Laue Lens (MLL) is a recent development in diffraction X-ray optics. An MLL includes a set of multilayers in transmission (Laue) geometry that is used for focusing the incident X-rays. FIGS. 1A-1C illustrate an example process of producing a one-dimensional (1D) MLL that corresponds to a linear zone plate. FIG. 1A illustrates an example coating process for creating a 1D MLL. A substrate 101 having a diameter between 10 to 100 mm is sputter coated with alternating layers of two materials 102, 103. For example, alternating opaque layers and transmissive layers that change the reflection angles of the incident light can be coated onto the substrate. In some embodiments, the first type of materials includes Tungsten (W), Molybdenum (Mo), Tungsten disilicide ($WSi_2$), and/or Platinum (Pt). The second type of materials includes Silicon (Si) and/or Carbon (C). Some example combinations of the two types of materials include (a) Tungsten/Silicon (W/Si), (b) Molybdenum/Silicon (Mo/Si), Tungsten disilicide/Silicon ($WSi_2$/Si), and Platinum/Carbon (Pt/C).

After the layers are coated onto the substrate, a slice 111 is extracted from the cylindrical deposited layers to form a lens element. FIG. 1B illustrates an example slice to be extracted to form a 1D MLL. FIG. 1C illustrates a schematic diagram of an extracted slice from the deposited layers. The extracted slice 111 can have a width between 0.5 to 100 mm and a height between 0.05 and 0.1 mm. The thickness of the slice ranges from 0.001 to 0.05 mm.

Figure 2:
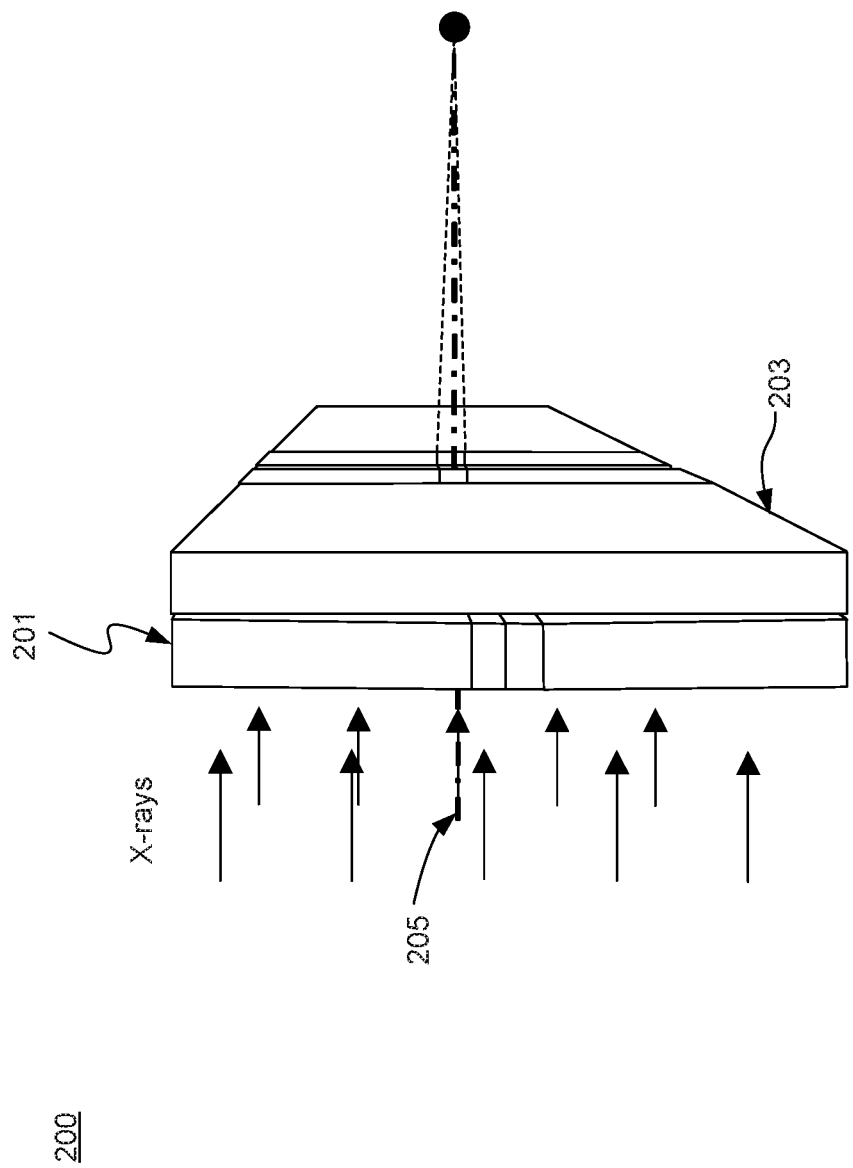
FIG. 2 illustrates a schematic diagram of an example two-dimensional (2D) multilayer Laue Lens (MLL) system.

A two-dimensional (2D) MLL that refracts rays in both x and y directions can be formed by positioning two pieces of 1D MLL substantially perpendicular to each other. FIG. 2 illustrates a schematic diagram of an example 2D MLL system 200. The 2D MLL system 200 includes two one-dimensional (1D) MLLs 201, 203 placed in series along an optical axis 205 and oriented perpendicularly with respect to each other. Each of the 1D MLL 201, 203 corresponds to a linear zone plate (as shown in FIGS. 1A-1C), which includes sections of multilayers that may vary in the deposition direction.

The development of MLL allows more versatile configurations of X-ray optical systems. In particular, a 2D MLL array of high numerical aperture and short focal length (e.g., 1-20 mm) can be created as a lens array for a light-field X-ray system.

Figure 3A:
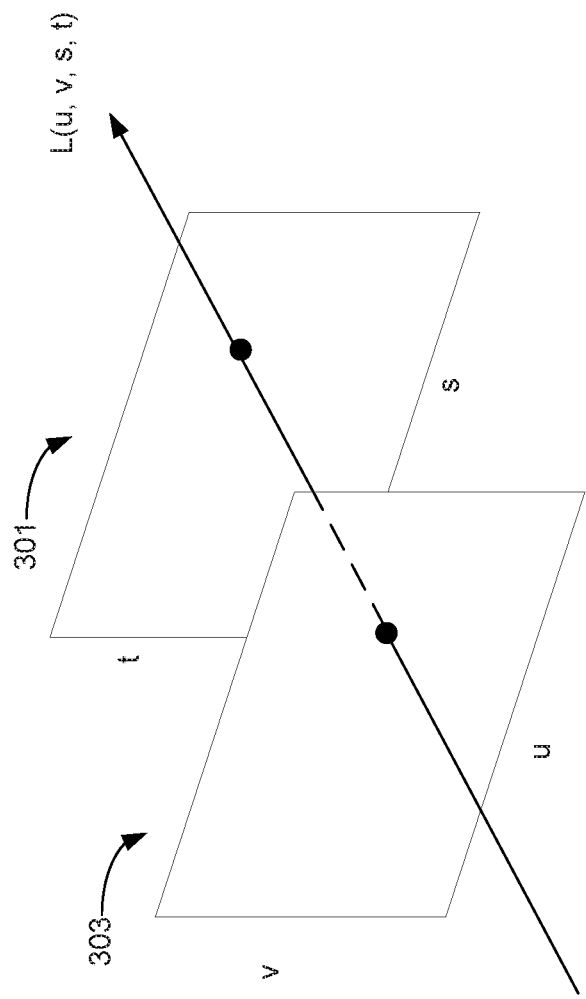
FIG. 3A is a schematic diagram illustrating a two-plane parameterization of a light field.

A light field is a vector function that describes the amount of light flowing in every direction through every point in space. The set of rays in a light field can be parameterized in a variety of ways. FIG. 3A is a schematic diagram illustrating a two-plane parameterization of a light field. A two-plane light field can be considered as a collection of perspective images of the st plane 301, each taken from an observer position on the uv plane 303. The two-plane parameterization has the advantage of relating closely to the analytic geometry of perspective imaging.

Figure 3B:
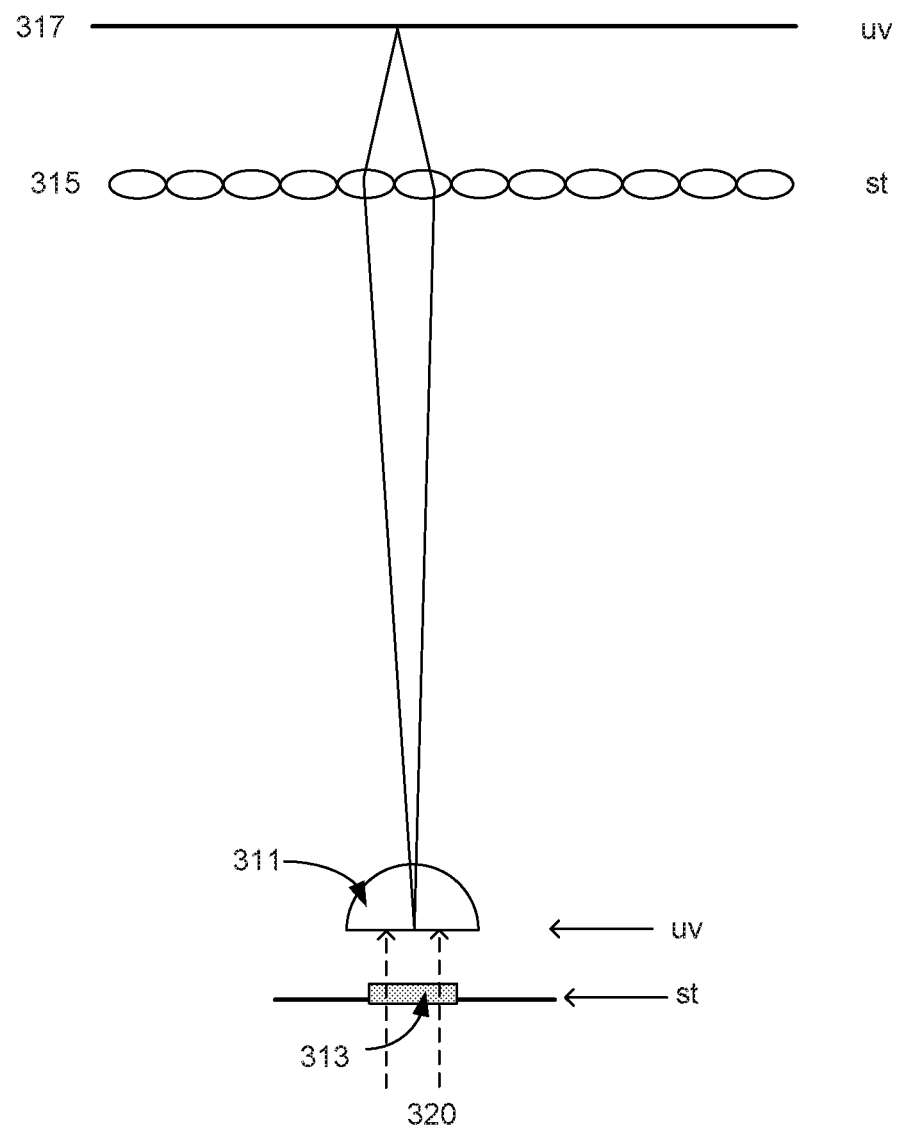
FIG. 3B illustrates a schematic diagram of an example light field microscopy configuration.

Light field microscopy (LFM) is a 3D microscopic imaging method based on the theory of light field. FIG. 3B illustrates a schematic diagram of an example light field microscopy configuration 300. As shown in FIG. 3B, a primary lens 311 is positioned along the optical paths of incoming light from a light source (e.g., X-ray) to image the target 313. A lens array 315 is placed at an intermediate image plane and a sensor 317 is placed behind it so that each microlens records an in-focus image of the target 313. The distance between the intermediate image plane and the sensor 317 can be in a range of 1 to 22 mm. When the incoming rays 320 are collimated, the intermediate image plane is at the focal plane of the primary lens 311 (or more generally the primary optics subsection). The primary lens 311 and the target 313 constitute the uv and st planes, and the sensor 317 and the microlens array 315 constitute a reimaging of these two planes. The light field can thus be captured by the microlens array 315, and the 3D structure of the target 313 can be computationally determined via 3D reconstruction.

Figure 4:
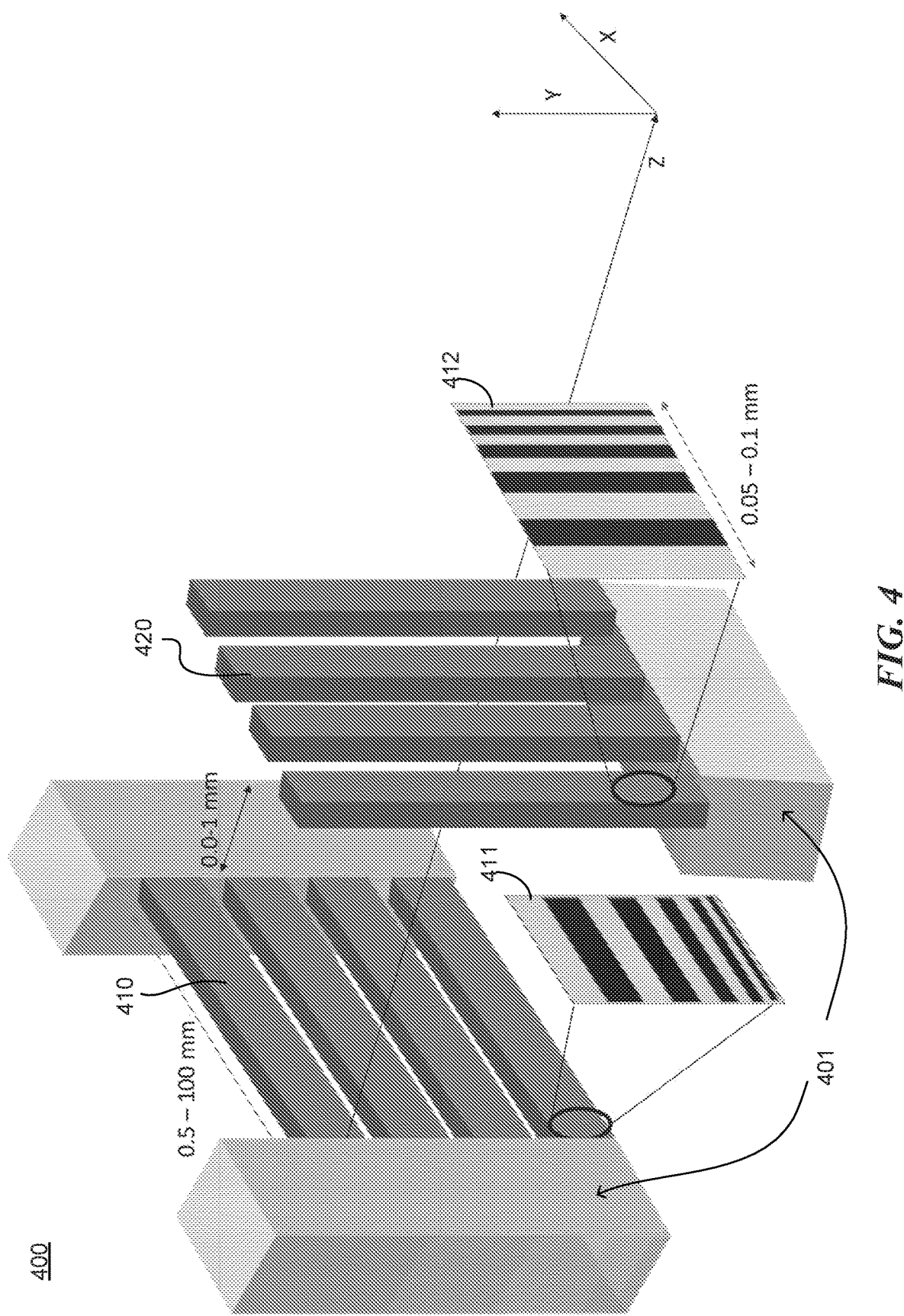
FIG. 4 illustrates a schematic diagram of an example MLL array in accordance with some embodiments of the present technology.

The lens array in a light-field optical system needs to have very short focal length to provide maximum divergence. FIG. 4 illustrates a schematic diagram of an example MLL array in accordance with some embodiments of the present technology. Here, an MLL array is constructed using a stack of 1D MLL 410 placed in a first direction and a stack of 1D MLL 420 placed in a second direction to form a 2D MLL array. The stacks can be secured to a support structure 401. Each lens element in the stack can have a length between 0.5 to 100 mm and a width between 0.05 to 0.1 mm. The two stacks are positioned in series along an optical axis (e.g., Z axis). The distance between the two stacks can range from 0 mm to 1 mm.

In some embodiments, all the lens elements of the first stack 410 in the first direction are identical to each other, and all the lens elements of the second stack 420 in the second direction are identical to each other. However, the lens elements in two stacks can be different—e.g., the layers in respective lens elements 411, 412 may have different thicknesses to direct the incoming X-rays into different angles.

Figure 5A:
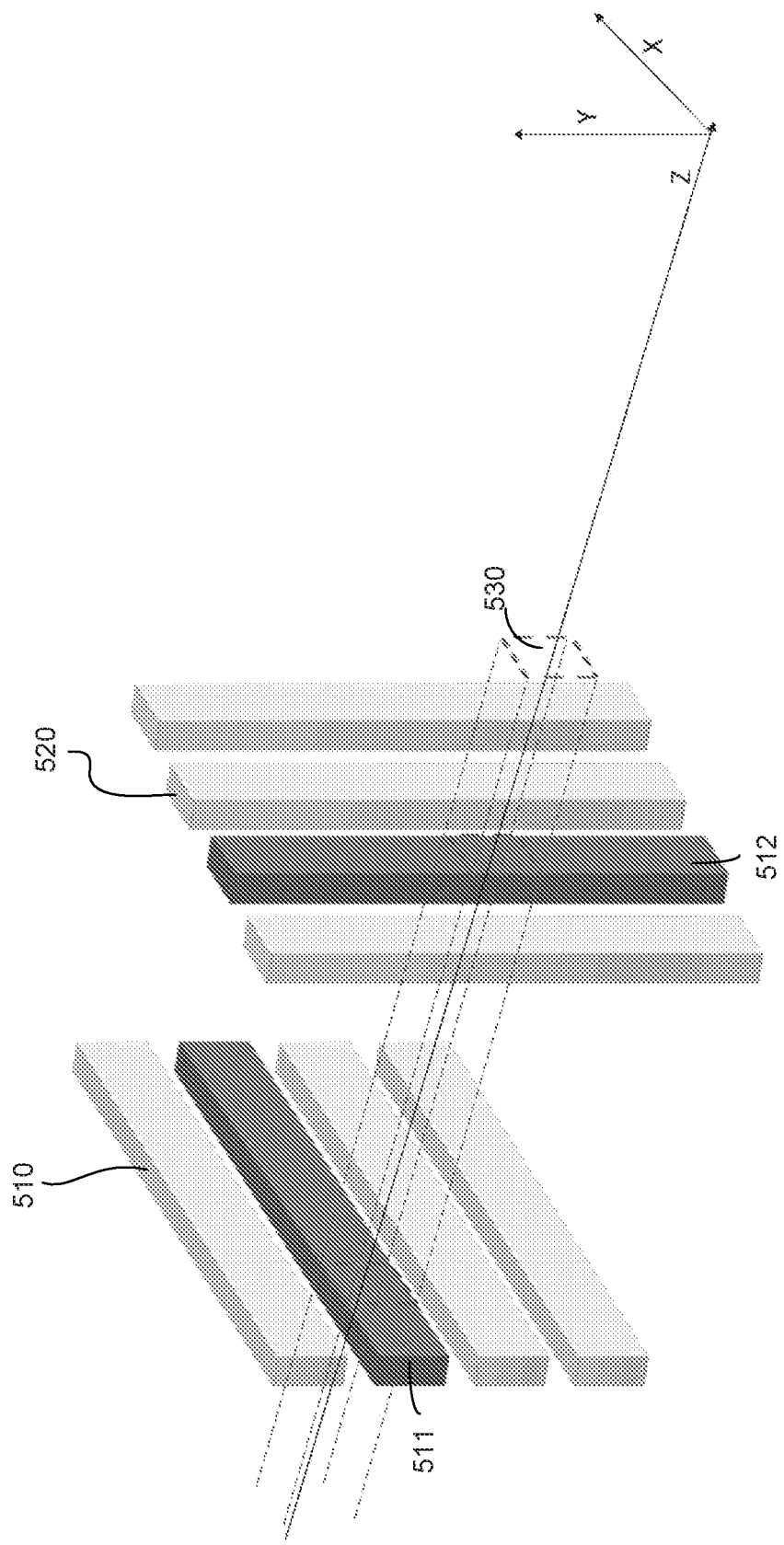
FIG. 5A illustrates an exploded view of an example lens array in accordance with the disclosed technology.
Figure 5B:
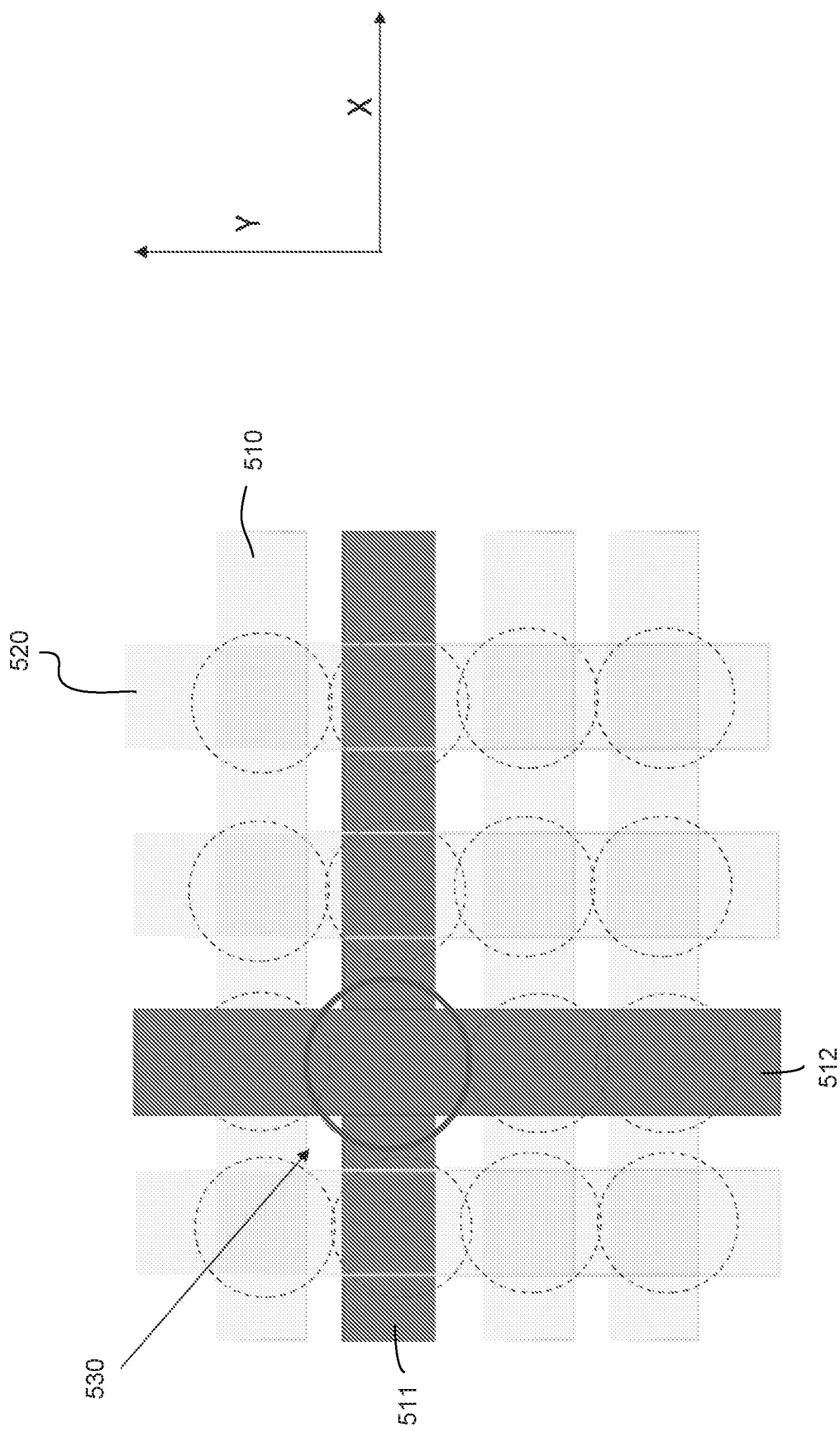
FIG. 5B illustrates a front view of the example lens array as shown in FIG. 5A in accordance with the disclosed technology.

FIG. 5A illustrates an exploded view of an example lens array in accordance with the disclosed technology. As shown in FIG. 5A, individual lens elements 511, 512 from the two stacks 510, 520 form an overlap area 530, which functions as a 2D MLL as depicted in FIG. 2. FIG. 5B illustrates a corresponding front view of the example lens array in accordance with the disclosed technology. The overlapped area 530 formed by individual lens elements 511, 512 functions as a 2D MLL to direct the light. All the overlapped areas thus form an array of MLLs to refract the incoming light (e.g., X-ray).

Figure 6A:
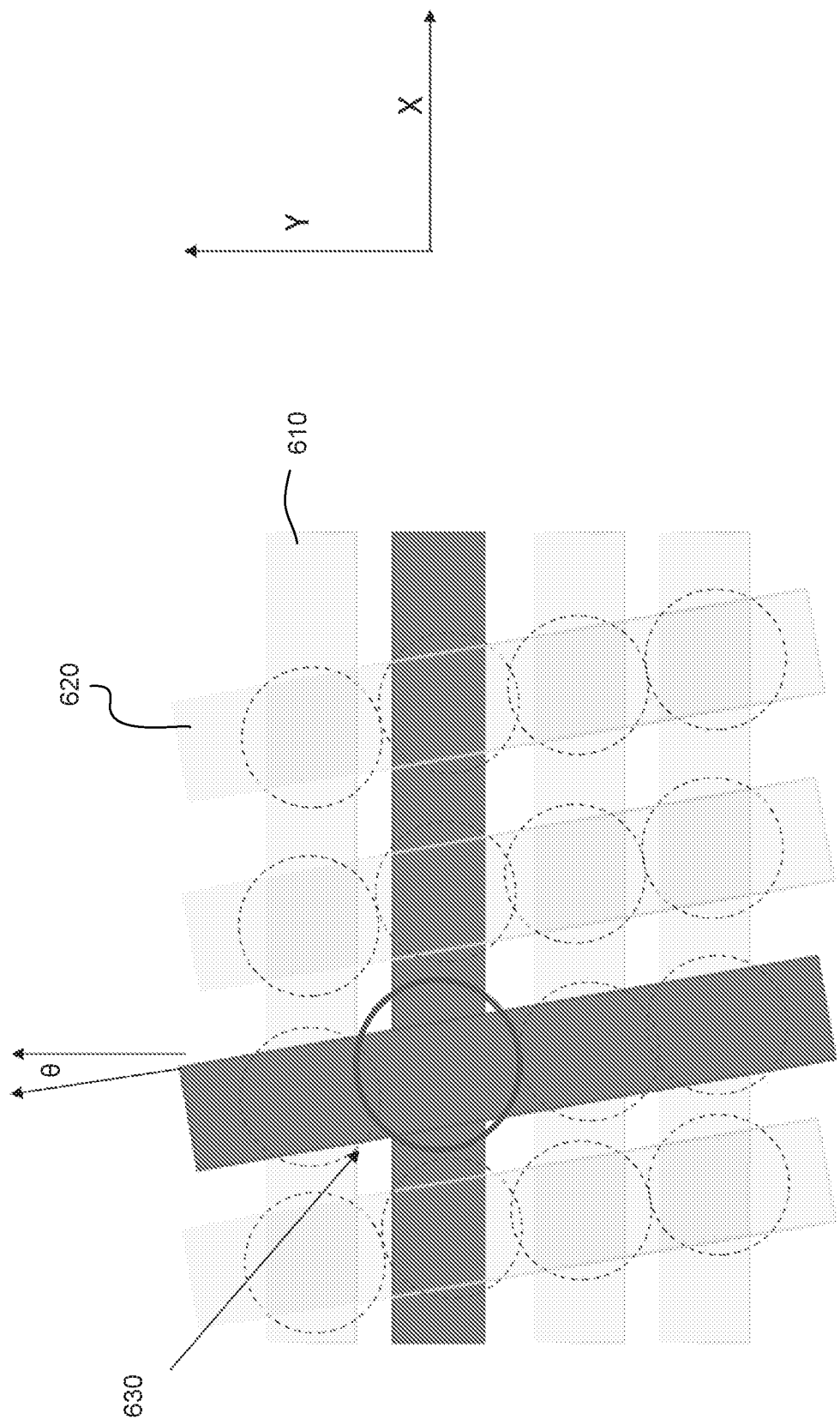
FIG. 6A illustrates an example misalignment in a lens array in accordance with the disclosed technology.
Figure 6B:
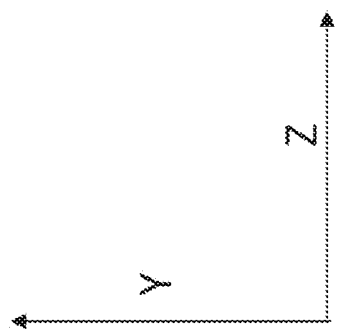
FIG. 6B illustrates another example misalignment in a lens array in accordance with the disclosed technology.
Figure 6B:
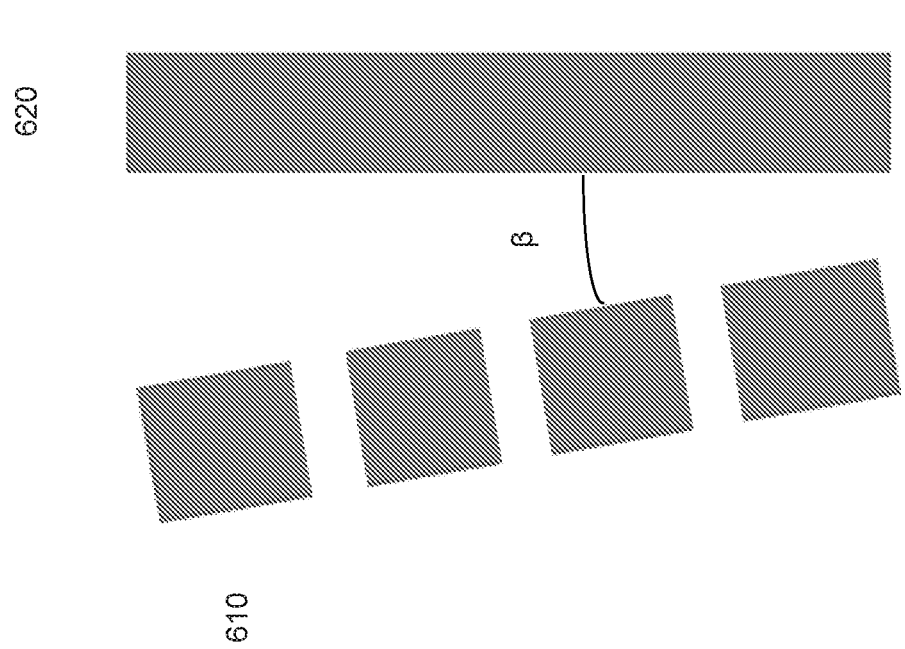

In some embodiments, the two stacks are positioned substantially orthogonal to each other. For example, one stack is placed horizontally, and the other stack is placed vertically, such as shown in FIG. 5B. In some implementations, however, a misalignment can occur when the lens array is constructed. FIG. 6A illustrates an example misalignment in a lens array in accordance with the disclosed technology. In this example, the two stacks 610, 620 are not perpendicular with respect to each other: a misalignment occurs in the x-y plane. To ensure optical performance of the overlapped area 630, the angle θ between the two stacks 610, 620 should be in a range between 0 to 10 degrees. FIG. 6B illustrates another example misalignment in a lens array in accordance with the disclosed technology. In this example, a misalignment occurs in the y-z plane—one stack is tilted at an angle β. Again, to ensure optical performance of the overlapped areas of the two tacks, the angle θ should be in a range between 0 to 10 degrees.

The example lens array in FIGS. 4-6B only include 16 array elements formed by four horizontal 1D lens elements and four vertical 1D MLL elements for illustrative purposes. In a practical configuration, the number of array elements can be proportional to the number of pixels of the sensor. In some implementations, the ratio between the number of pixels of the sensor to the number of lens array elements along the same dimension is around 3:1. For example, when the sensor has around 1000 pixels along one dimension, the lens array can have around 300 lens elements along the same dimension. In some embodiments, the thickness of each lens element is between 5 to 15 microns. The focal length of the MLL array is typically within a range of 1 to 22 mm, but longer focal lengths can also be supported.

The 2D MLL arrays can be designed to produce a particular focal length for X-rays of particular energy. Because each 1D MLL corresponds to a linear zone plane, each layer in the 1D MLL forms a "zone." The thickness of each layer can be determined by the X-ray wavelength, the desired focal length, and the zone number of the layer:

$$r_n^2 = n\lambda\left(f + \frac{n\lambda}{4}\right).$$

Figure 7A:
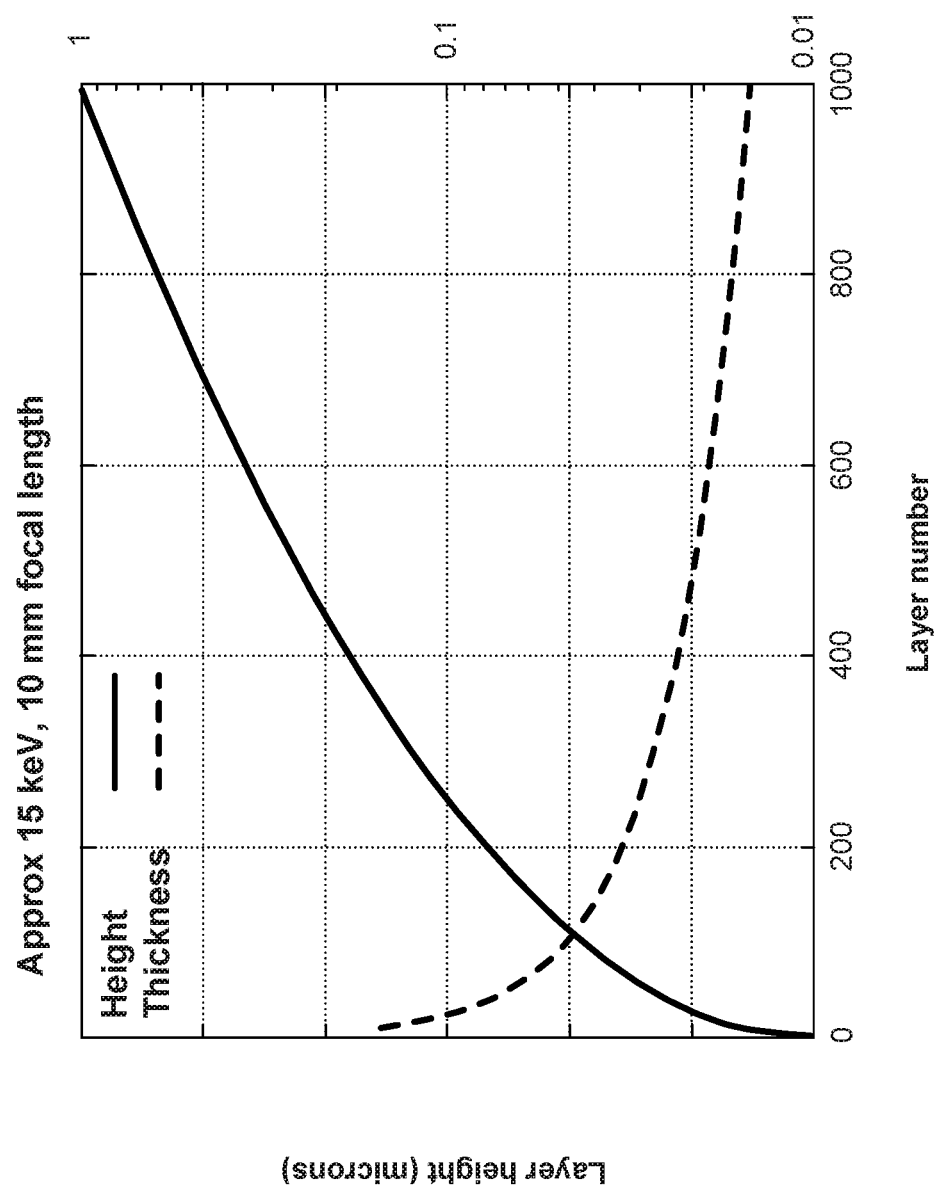
FIG. 7A illustrates a plot showing layer thicknesses of an example lens array in accordance with some embodiments of the present technology.
Figure 7B:
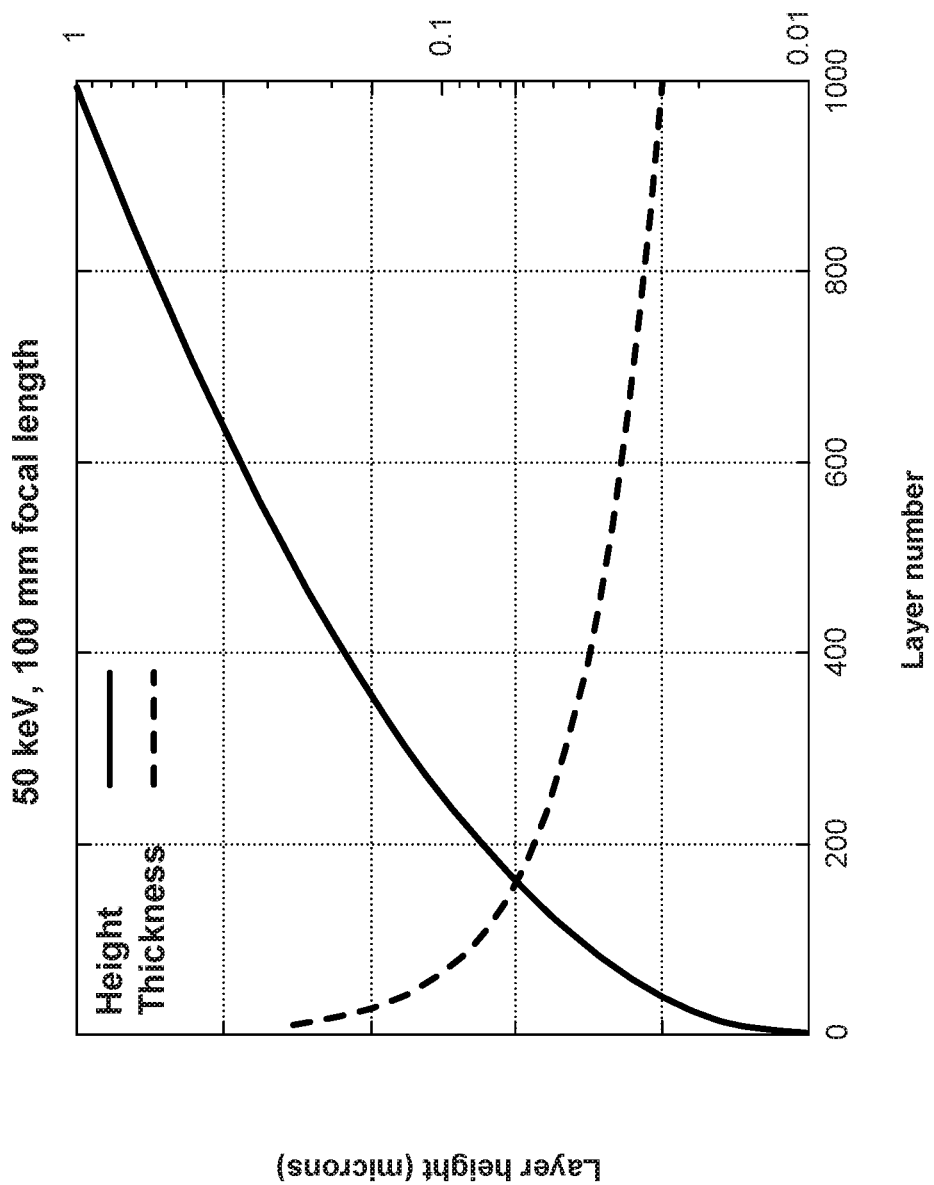
FIG. 7B illustrates a plot showing layer thicknesses for an example lens array in accordance with some embodiments of the present technology.

FIG. 7A illustrates a plot showing layer thicknesses of an example MLL array in accordance with some embodiments of the present technology. In this example, the MLL array is designed to have a focal length of 10 mm and operate with X-rays having an energy of 15 keV. The first layer of the MLL lens element is relatively thick (e.g., thicker than 0.1 microns). As the number of layers increases, the thicknesses of the layers decrease. FIG. 7B illustrates a plot showing layer thicknesses for another example MLL array in accordance with some embodiments of the present technology. In this example, the MLL array is designed to have a focal length of 100 mm at X-ray energy level of 50 keV. Similar to the example shown in FIG. 7A, the thicknesses of the layers decrease as the number of layers increases.

Figure 13:
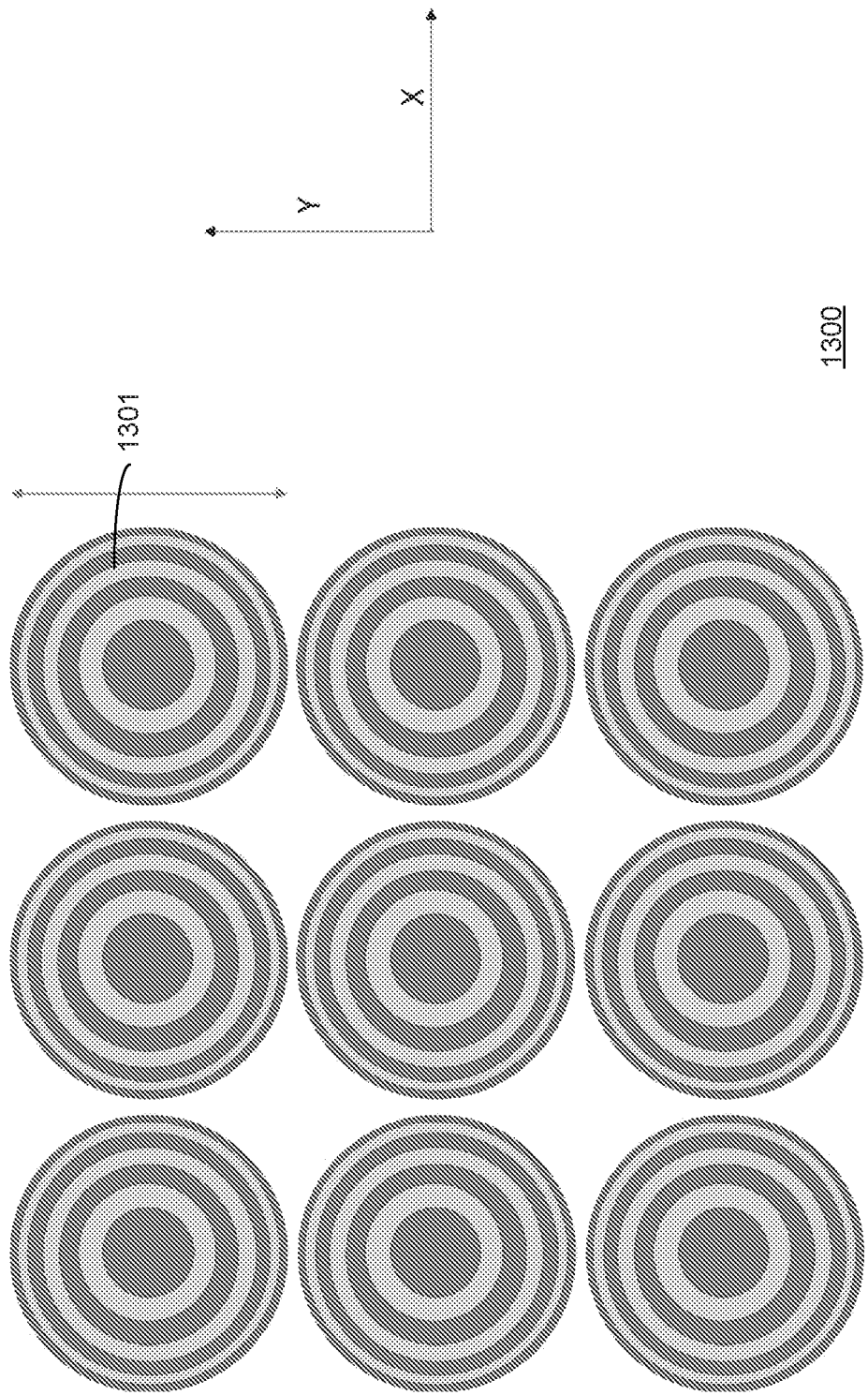
FIG. 13 illustrates a top view of another example lens array in accordance with some embodiments of the present technology.

FIG. 13 illustrates a top view of another example lens array 1300 in accordance with some embodiments of the present technology. In this example, each of the lens elements 1301 in the array is a Fresnel zone plate, which can have a diameter in a range of 0.01 to 0.2 mm and a thickness in a range of 0.1 to 5 μm. Similarly, in a practical configuration, the number of array elements can be proportional to the number of pixels of the sensor. In some implementations, the ratio between the number of pixels of the sensor to the number of lens array elements along the same dimension is around 3:1. For example, when the sensor has around 1000 pixels along one dimension, the lens array can have around 300 zone plate elements along the same dimension.

Figure 14A:
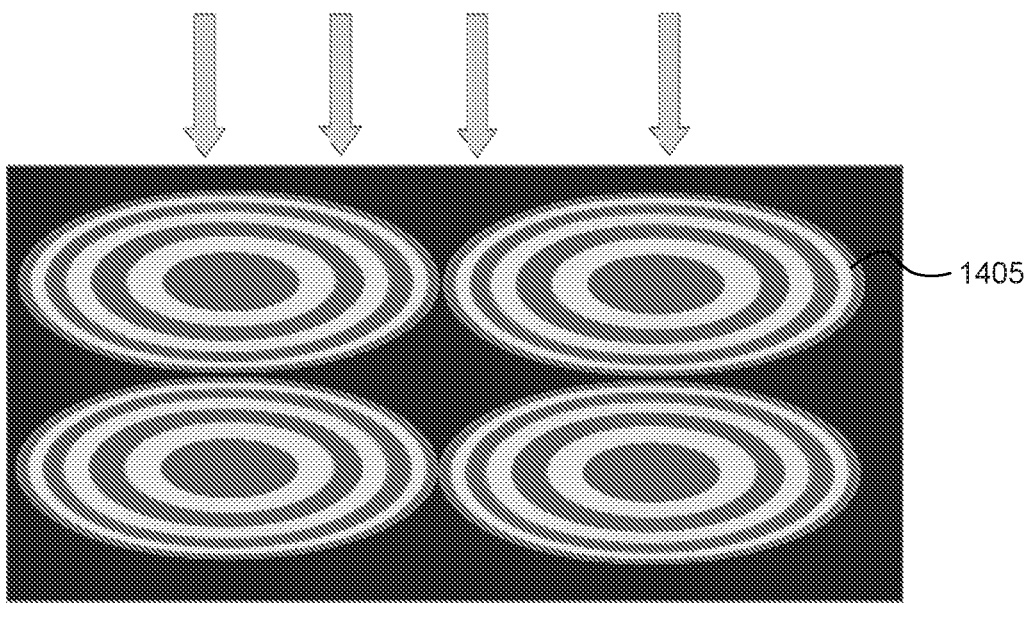
FIG. 14A illustrates an example mask, substrate, and resist for a lithography fabrication process of a zone plate array in accordance with some embodiments of the present technology.
Figure 14A:
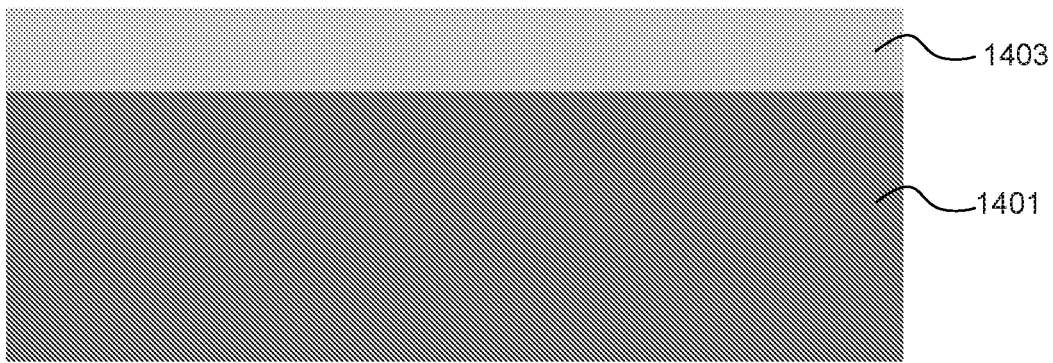
Figure 14B:
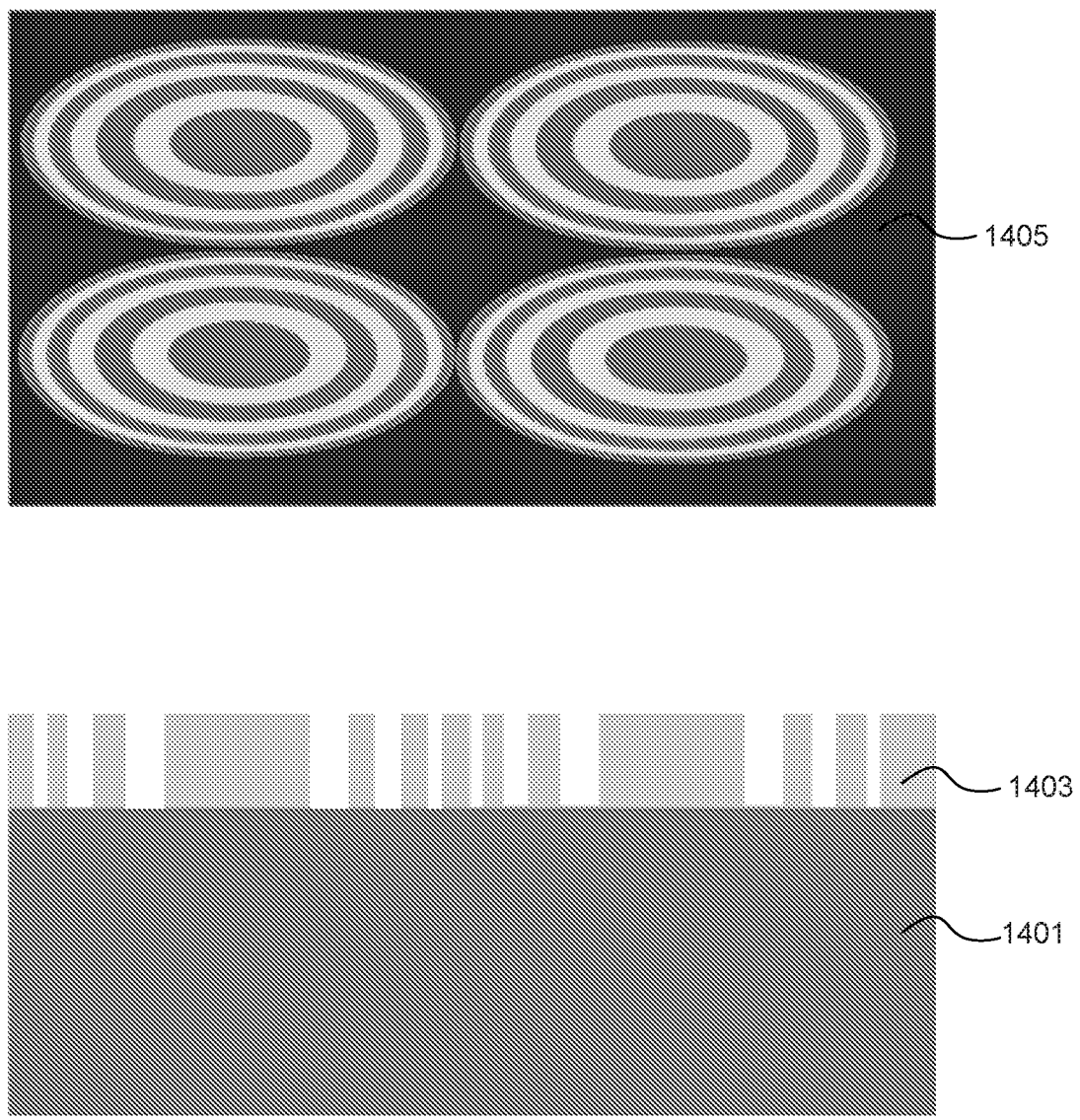
FIG. 14B illustrate an example resist after being exposed to a radiation source in accordance with some embodiments of the present technology.
Figure 14C:
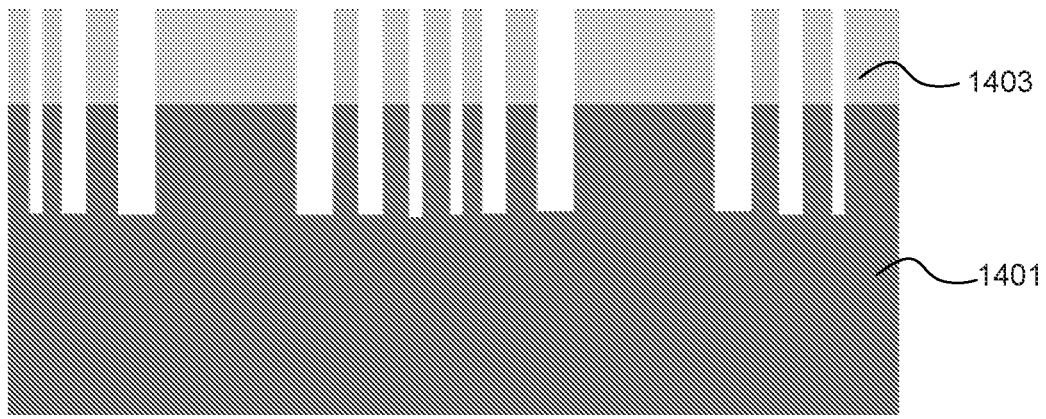
FIG. 14C illustrates an example etched substrate in accordance with some embodiments of the present technology.
Figure 14D:
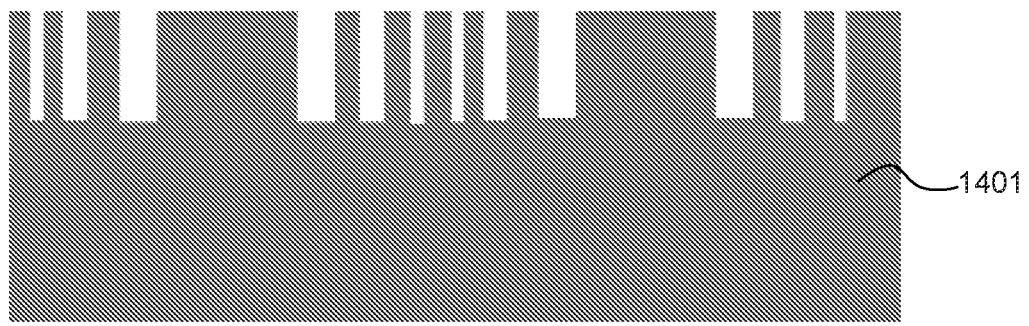
FIG. 14D illustrates an example etched substrate with a resist removed in accordance with some embodiments of the present technology.
Figure 14E:
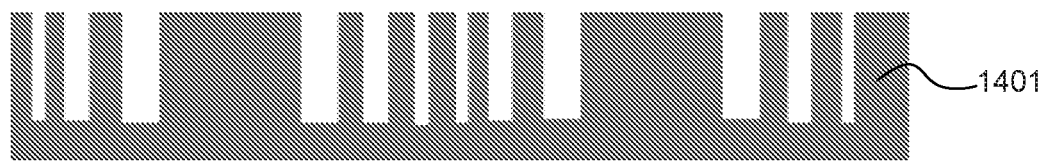
FIG. 14E illustrates an example thinned substrate in accordance with some embodiments of the present technology.
Figure 14F:
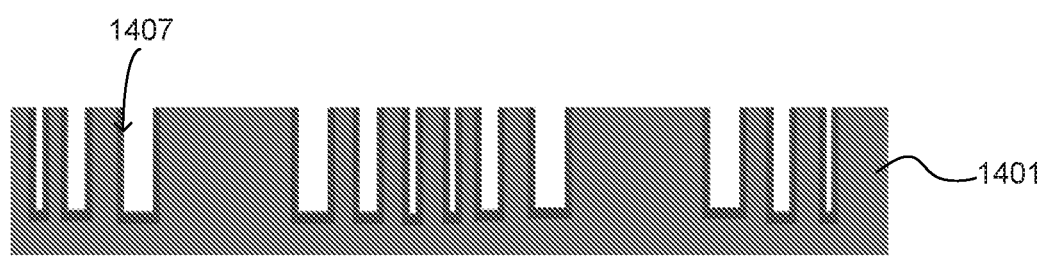
FIG. 14F illustrates an example substrate with a deposited material in accordance with some embodiments of the present technology.

As compared to the 2D MLL array, fabrication of the zone plate array is easier—the entire array can be fabricated at the same time using the photo-lithography process. FIGS. 14A-14F illustrate an example fabrication process of a zone plate array in accordance with some embodiments of the present technology. As shown in FIG. 14A, a substrate 1401 is coated with a layer of a light-sensitive chemical photoresist (or simply "resist") 1403. A mask 1405, which can absorb a part of a radiation source and allow a part of the radiation source to go through, is used to define the desired pattern of the entire zone plate array. The mask 1405, the resist 1403, and the substrate 1401 are then exposed to a radiation source (e.g., electrons, X-rays, ions, etc.). FIG. 14B illustrates that the radiation source transfers the geometric pattern from the photomask 1405 to the resist 1403 on the substrate 1401. Depending on the composition of the resist 1403, as shown in FIG. 14C, the pattern can be etched into the substrate 1401. The resist 1403 is then removed (as shown in FIG. 14D) and the substrate 1401 can be thinned (as shown in FIG. 14E). FIG. 14F illustrates an example step to deposit material(s) 1407 onto the substrate 1401 if necessary. As compared to the 2D MLL array, the focal length of the zone plate array may be more limited. The zone plate array is more suitable for X-ray energies that are lower than 10 keV, while the 2D MLL array can be work with a higher X-ray energy level.

With reference to FIGS. 3A-3B, the range of the angles of the incoming light from the target 313 that is collected by the primary lens 311 depends on the distance between the primary lens 311 and the target 313—a shorter distance leads to a wider range of angles. The lens array 315 (e.g., as constructed using a 2D MLL array) separates out the different angles and reimages them onto different sensor 307 elements—that is, the spatial information is spread into both spatial and angular information by the lens array 315. For example, the example 2D MLL shown in FIG. 4 can be positioned on the optical axis at the position of the lens array 315; in this configuration, the incoming rays go through 16 elements and are reimaged on the sensor that is positioned at plane 317 in FIG. 3. The resulting image can be computationally analyzed to trace the rays back to the target, thereby determining the 3D shape of the target.

A variety of X-ray optics can be used as the primary optics in the disclosed light field X-ray systems. Several reflective optic configurations have been developed in the past. For example, Schwarzschild optics includes two spherical mirrors and can be used for soft X-rays and for extreme ultraviolet light. However, it does not work for higher photon energies because the light is reflected early under 90 degrees. Kirkpatrick-Baez optics (KB optics) also includes two mirrors. The KB optics, however, is expensive and heavy and do not fulfill the Abbe criterion.

Figure 8A:
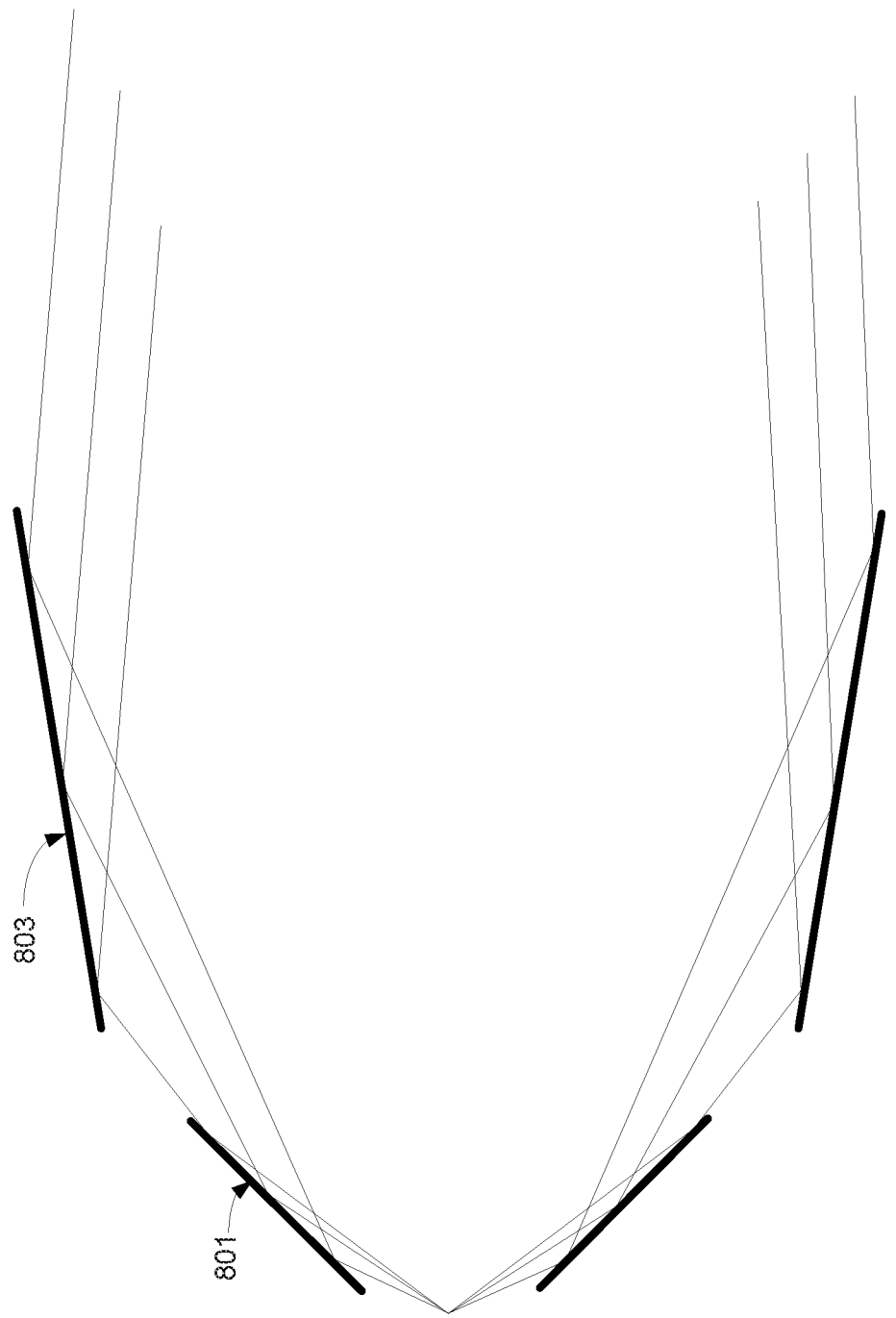
FIG. 8A illustrates example optical paths of the Wolter Type 1 optics.

Wolter optics (hereinafter sometimes referred to as a Wolter lens) includes a set of nested mirrors arranged concentrically to the optical axis. FIG. 8A illustrates example optical paths for a Wolter Type 1 optics. By using two mirrors 801 and 803, it is possible to create an optical lens with a usable field of view (e.g., between 1×1 mm to 5×5 mm at the focal plane). In some embodiments, the Wolter lens can have a diameter ranging from 25 mm to 200 mm and a length between 50 to 400 mm. The focal length of the Wolter lens can be in a range of 200 mm to 1 m.

It is noted that the Wolter lens has a short depth of field, typically ranging from 1 mm down to 100 microns. As a result, target objects can go out of focus quickly over a few millimeters, which makes the Wolter lens not a particularly desirable lens for producing images in conventional optical settings. However, such an attribute also allows efficient capture of the light field when coupled with an MLL lens array.

Figure 8B:
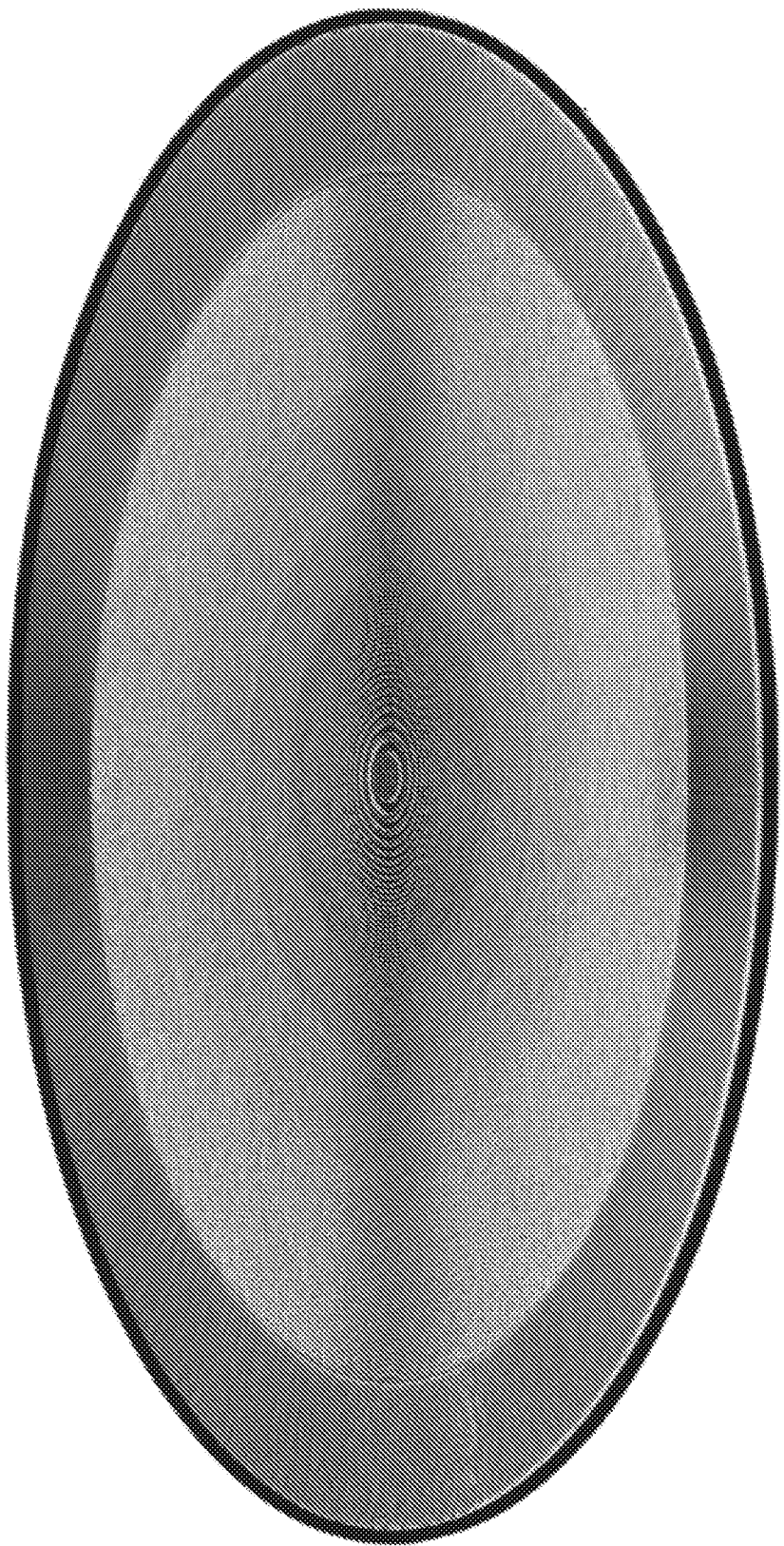
FIG. 8B illustrates a Scanning Electron Microscope (SEM) image of an example hard X-Ray 25-nm resolution zone plate.

Besides Wolter optics, other types of optical systems can be used as the primary optics in the light-field X-ray configuration. For example, a 2D MLL can be used as the primary optics to allow a shorter working distance between the lens and the target object. In some embodiments, a zone plate can be used as the primary optics because it provides a larger depth of field suitable for imaging larger target. FIG. 8B illustrates an SEM Image of hard X-Ray 25 nm resolution zone plates that can be used as the primary optics.

Figure 9:
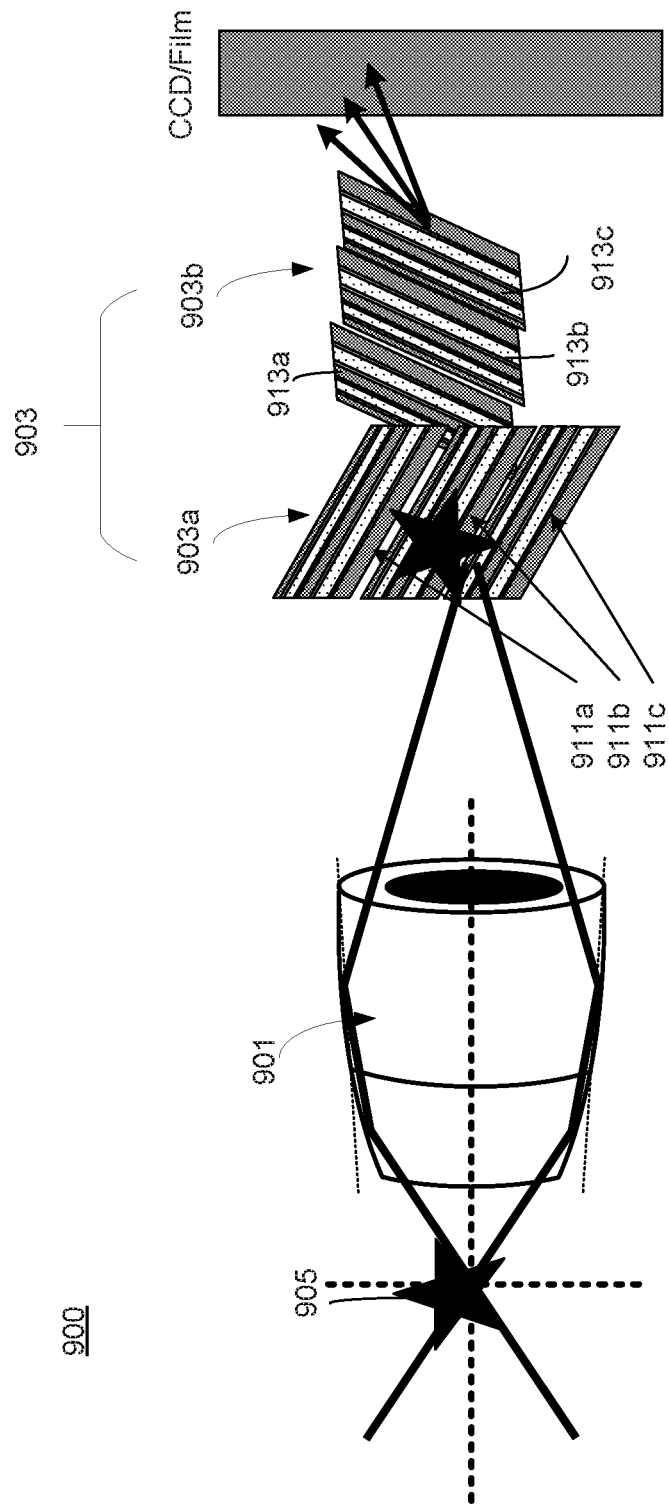
FIG. 9 illustrates an example light field X-ray system in accordance with some embodiments of the present technology.

FIG. 9 illustrates an example light field X-ray system 900 in accordance with the disclosed technology. In this embodiment, the primary optics includes a Wolter lens 901. An MLL array 903 that includes two 1D MLL panels is placed close to the focal plane of the Wolter lens 901 to capture the light field. The numerical aperture of the MLL array 903 covers the range of angles from the Wolter optics 901, which can be from 0.1 to 5 degrees.

In some embodiments, each of 1D MLL includes multiple lens elements (e.g., 911a, 911b, 911c, 913a, 913b, 913c). The first 1D MLL 903a includes lens elements that are oriented in a first direction (e.g., horizontally placed elements). The second 1D MLL 903b includes lens elements that are oriented in a second direction (e.g., the vertically placed elements). The first and the second 1D MLLs are generally positioned at the focal plane of the primary optics. In some embodiments, the first 1D MLL is positioned before the focal plane of the Wolter lens 901 while the second 1D MLL is positioned after the focal plane. In some embodiments, one of the first or the second 1D MLL is positioned at the focal plane, while the other of first or the second 1D MLL is positioned before or after the focal plane. The distance between the two 1D MLLs ranges from 0 to 1 mm. In these configurations, the lens elements can be designed to take into account the intended placement of the 1D MLLs. For example, in configurations where one of the 1D MLL is positioned at the focal plane, the two 1D MLLs may need to have different designs (e.g., different number of layers and/or thicknesses) to provide the desired imaging characteristics. In some embodiments, the two 1D MMLs are identical, which may provide the desired imaging characteristic for some applications. The 1D MLLs can be arranged close to the sensor film or the Charged Coupled Device (CCD). For example, the MLL array 903 can be parallel to the film or the CCD. The array can also be tilted relative to the film or the CCD.

Due the nature of grazing incident angles, the Wolter lens has a small field of view and thus is placed further from the target object 905. In some embodiments, the working distance between the Wolter lens 901 and the object 905 is around 500 mm. One major advantage of the Wolter mirrors is its large angular collection area, which allows the optical system to collect more photons from the incoming rays.

Figure 10:
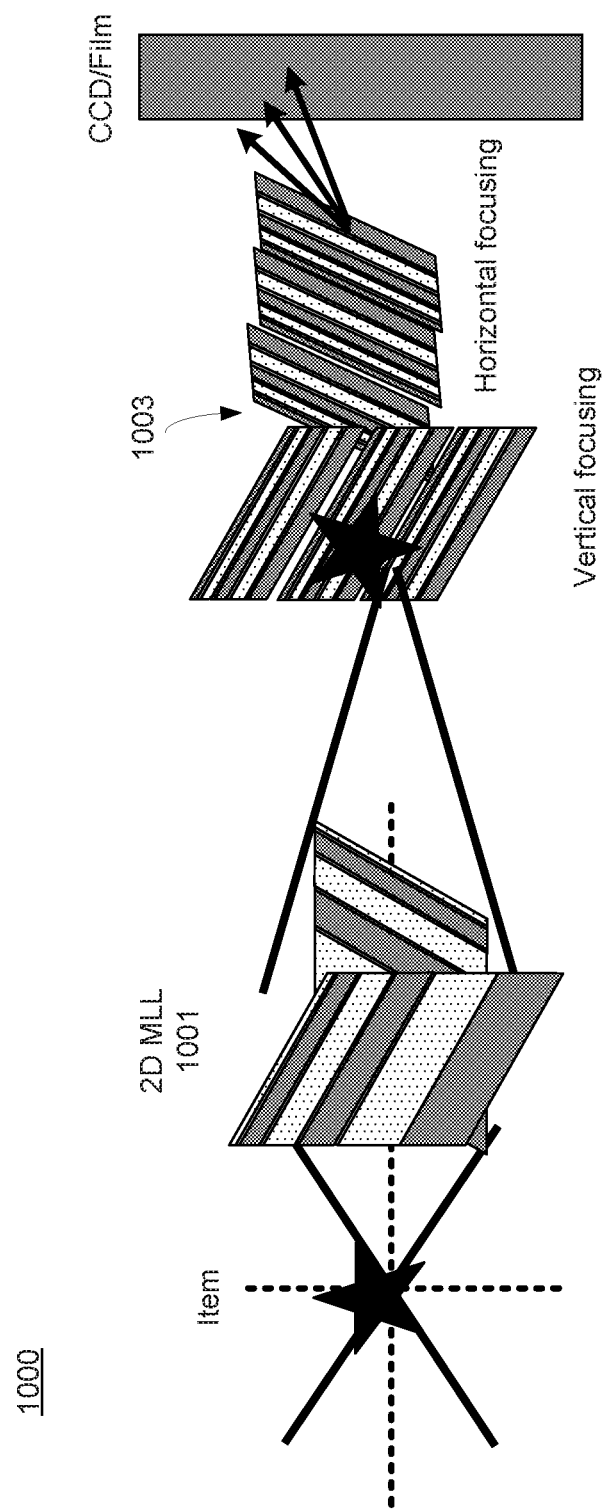
FIG. 10 illustrates another example X-ray light field configuration in accordance with some embodiments of the present technology.

FIG. 10 illustrates an example X-ray light field system 1000 in accordance with some embodiments of the present technology. In the depicted configuration, the primary optics section includes a 2D MLL 1001. The MLL array 1003 can be arranged in a similar way as shown in FIG. 9. In some embodiments, the primary 2D MLL 1003 can have the same size as the MLL array 1001. The primary 2D MLL 1001 has a short focal length as compared to the Wolter lens. This allows a much shorter working distance that is between 1 to 100 mm. The primary 2D MLL 1001 can also be constructed at a lower cost as compared to the Wolter lens.

Figure 11:
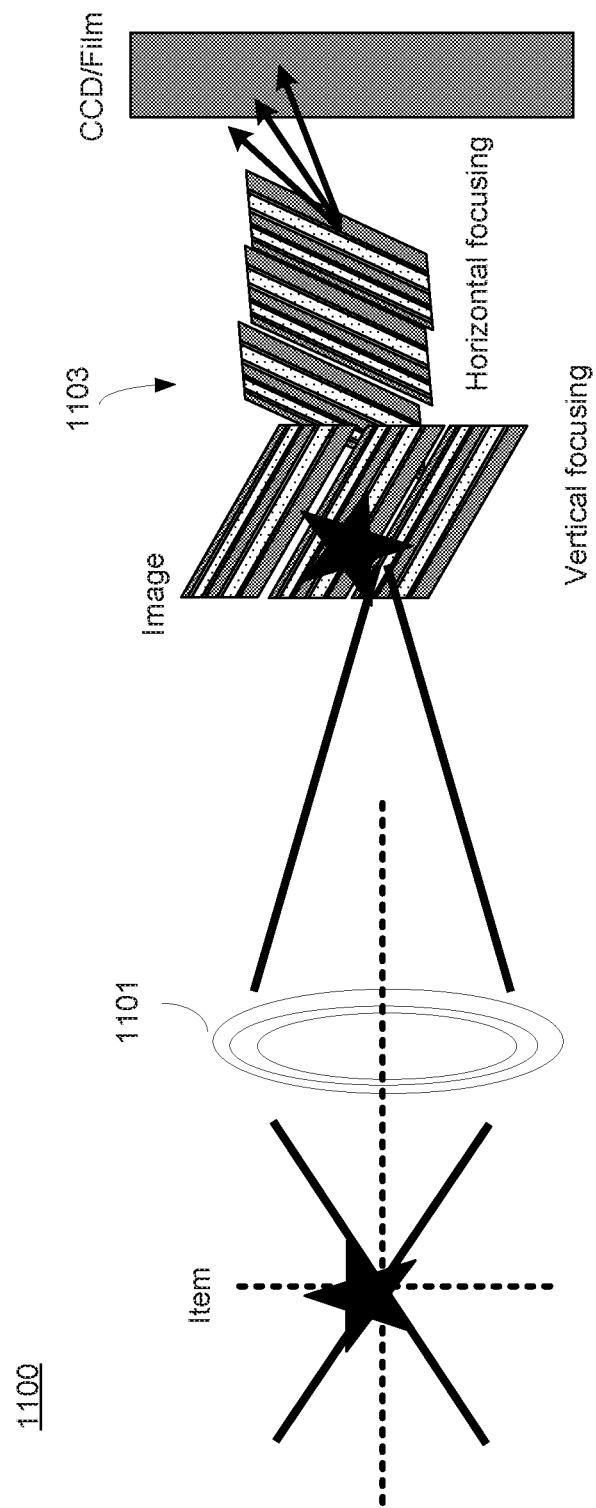
FIG. 11 illustrates yet another example X-ray light field configuration in accordance with some embodiments of the present technology.

FIG. 11 illustrates an example X-ray light field system 1100 in accordance with some embodiments of the present technology. In the depicted configuration, the primary optics section includes a zone plate 1101. The MLL array 1103 can be similar to, and arranged in a similar way, as shown in FIG. 9. As compared to the Wolter lens, the zone plate 1101 has a larger depth of field, which makes this configuration more suitable for imaging larger objects.

Figure 12:
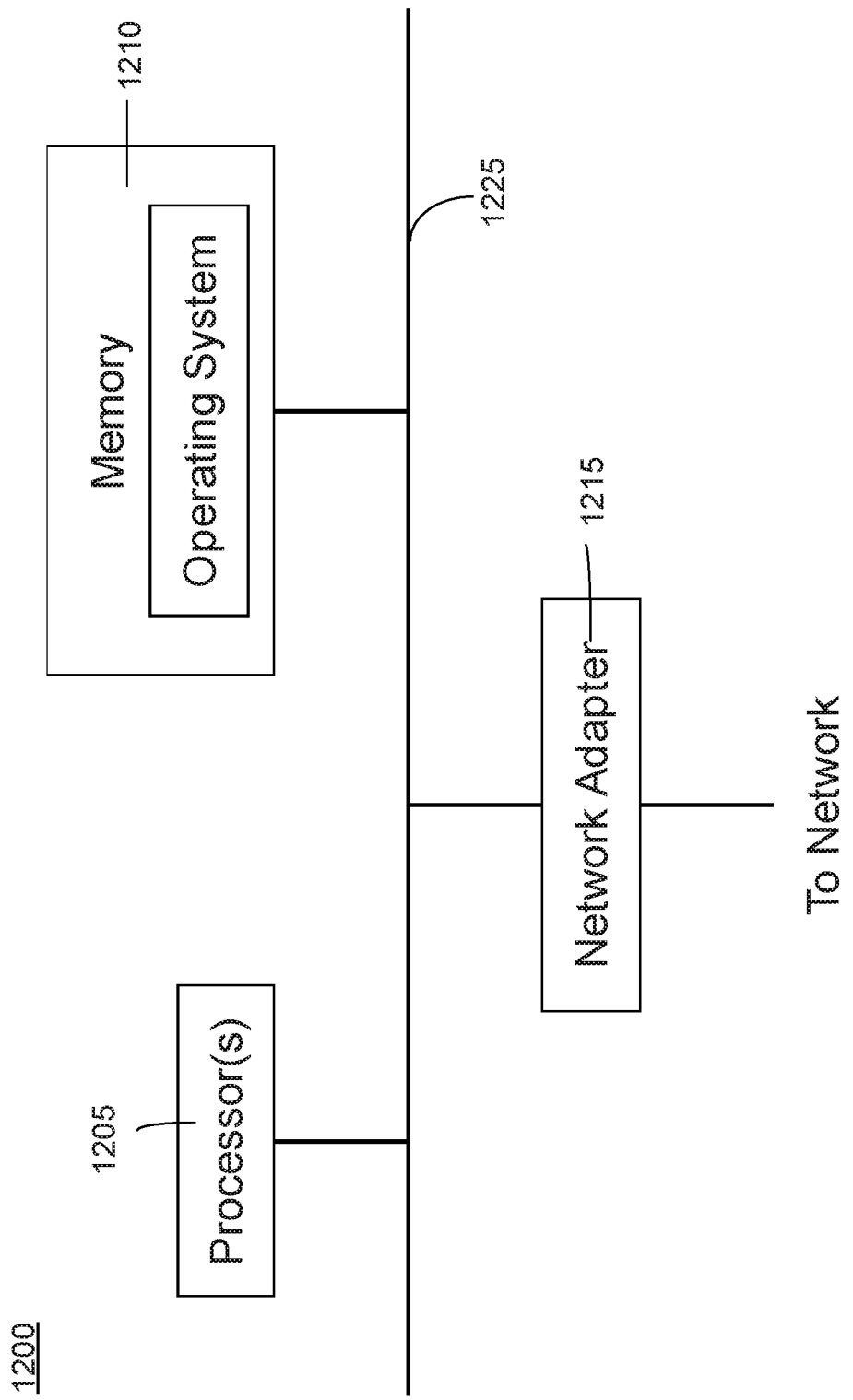
FIG. 12 is a block diagram illustrating an example of the architecture for a computer system or other control device that can be utilized to implement various portions of the presently disclosed technology.

FIG. 12 is a block diagram illustrating an example of the architecture for a processing system 1200 can be utilized to implement various portions of the presently disclosed technology. In FIG. 12, the processing system 1200 includes one or more processors 1205 and memory 1210 connected via an interconnect 1225. The processing system 1200 can further be coupled to the CCD as shown in FIGS. 8-10 via the interconnect 1225. The processing system 1200 can received electrical signals or associated information from the CCD and performs a tomography or 3D reconstruction algorithm to determine a three-dimensional (3D) structure of the object. The relationship between three-dimensional imaging by an optical system and by a tomographic imaging system has been stated in the related art. For examples, algorithms that use constrained gradient descent (also referred to as constrained iterative deconvolution or Simultaneous Algebraic Reconstruction Technique (SART)) can be used to obtain 3D reconstruction of the object.

The interconnect 1225 may represent any one or more separate physical buses, point to point connections, or both, connected by appropriate bridges, adapters, or controllers. The interconnect 1225, therefore, may include, for example, a system bus, a Peripheral Component Interconnect (PCI) bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 674 bus, sometimes referred to as "Firewire."

The processor(s) 1205 may include central processing units (CPUs) to control the overall operation of, for example, the host computer. In certain embodiments, the processor(s) 1205 accomplish this by executing software or firmware stored in memory 1210. The processor(s) 1205 may be, or may include, one or more programmable general-purpose or special-purpose microprocessors, digital signal processors (DSPs), programmable controllers, application specific integrated circuits (ASICs), programmable logic devices (PLDs), or the like, or a combination of such devices.

The memory 1210 can be or include the main memory of the computer system. The memory 1210 represents any suitable form of random access memory (RAM), read-only memory (ROM), flash memory, or the like, or a combination of such devices. In use, the memory 1210 may contain, among other things, a set of machine instructions which, when executed by processor 1205, causes the processor 1205 to perform operations to implement embodiments of the presently disclosed technology.

Also connected to the processor(s) 1205 through the interconnect 1225 is a (optional) network adapter 1215. The network adapter 1215 provides the computer system 1200 with the ability to communicate with remote devices, such as the storage clients, and/or other storage servers, and may be, for example, an Ethernet adapter or Fiber Channel adapter.

The use of the MLL array allows a light field to be captured at the film or CCD, thereby providing a three-dimensional structure of the target item once the light field is reconstructed. The internal structure of the target item can thus be obtained using a single line of sight without rotating or moving the target item. Dynamic experiments requiring repeated measurements can thus be performed with ease due to the short measurement process.

In one example aspect, a light field X-ray optical system is disclosed. The system includes a primary optics subsection positioned to receive incoming X-rays after traversal through an object and to redirect the received incoming X-rays onto an intermediate image plane. The system also includes a microlens array positioned at or close to the intermediate image plane to receive at least some of the received incoming X-rays after redirection by the primary optics subsection to diffract the X-rays that are incident thereupon.

In some embodiments, the intermediate image plane coincides with a focal plane of the primary optics subsection. In some embodiments, the microlens array comprises a first set of multilayer Laue lenses (MLLs) having multiple layers of X-ray refractive material arranged in a first direction to diffract the redirected X-rays that are incident thereupon, and a second set of MLLs having multiple layers of X-ray refractive material arranged in a second direction to receive X-rays after diffraction by the first set of MLLs. In some embodiments, the multiple layers of first set of MLLs are separated from one another at different spacing values. In some embodiments, a distance between the first set of MLLs and the second set of MLLs is in a range between 0 to 1 mm. In some embodiments, one or both of the first set of MLLs or the second set of MLLs is positioned at an offset from an exact location of the intermediate image plane. In some embodiments, one or both a number of layers or a spacing between the layers in the first set of MLLs is different from a number of layers or a spacing between the layers in the second set of MLLs. In some embodiments, the first direction is substantially perpendicular to the second direction. In some embodiments, an angle between the first direction and the second direction is in a range of 80 degrees to 100 degrees. In some embodiments, thicknesses of the layers in of the first set and the second set of MLLs are determined based on a predetermined focal length value of the microlens array and an energy of the incoming X-rays.

In some embodiments, the microlens array comprises an array of zone plates. In some embodiments, each zone plate in the array of zone plates has a diameter in a range of 0.01 to 0.2 mm. In some embodiments, wherein each zone plate in the array of zone plates has a thickness in a range of 0.1 to 5 µm.

In some embodiments, the primary optics subsection includes a Wolter lens configured to receive the incoming X-rays at grazing incident angles. The Wolter lens has a diameter in a range 25 mm to 200 mm and a length in a range 50 mm to 400 mm. In some embodiments, the Wolter lens has a focal length in a range 200 mm to 1 meter.

In some embodiments, the primary optics subsection includes a third set of MLLs arranged in a third direction and a fourth set of MLLs arranged in a fourth direction, the third and four directions being substantially perpendicular to each other. In some embodiments, the primary optics subsection includes a zone plate.

In some embodiments, the system further includes a pixelated detector positioned at a focal plane of the microlens array to receive X-rays from the micro lens array and to produce electrical signals or associated information in response thereto. In some embodiments, the system also includes a processing system coupled to the pixelated detector to receive the electrical signals or associated information and to determine a three-dimensional structure of the object.

In another example aspect, a lens array for use in a light field X-ray microscopy system is disclosed. The lens array includes a first set of multilayer Laue lenses (MLLs) positioned side-by-side in first plane, each MLL in the first set including a set of layers arranged in a first direction. The lens array also includes a second set of MLLs positioned side-by-side in a second first plane, each MLL in the second set including a set of layers arranged in a second direction. The first and the second plane are selected to allow the first set of MLLs to receive an incoming X-ray beam and to redirect the incoming X-ray beam, and the second set of MLLs to receive the redirected X-ray beam onto a focal plane of the lens array. Numbers and thicknesses of the set of layers in the first set of MLLs and in the second set of MLLs are selected to produce a predetermined focal length for the lens array for a given energy level of the incoming X-ray beam. In some embodiments, the first direction is substantially perpendicular to the second direction. In some embodiments, an angle between the first direction and the second direction is in a range 80 degrees to 100 degrees.

At least parts of the disclosed embodiments that include modules and the functional operations can be implemented in digital electronic circuitry, or in computer software, firmware, or hardware. For example, electronic circuits can be used to control the operation of the detector arrays and/or to process electronic signals that are produced by the detectors. At least some of those embodiments or operations can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Computer-readable media suitable for storing computer program instructions and data include all forms of non-volatile memory, media and memory devices, including, by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

The invention claimed is:

1. A light field X-ray optical system, comprising:
a primary optics subsection positioned to receive incoming X-rays after traversal through an object and to redirect the received incoming X-rays onto an intermediate image plane that coincides with a focal plane of the primary optics subsection; and
a microlens array positioned at the intermediate image plane to receive at least some of the received incoming X-rays after redirection by the primary optics subsection to diffract the X-rays that are incident thereupon.

2. The light field X-ray optical system of claim 1, wherein the microlens array comprises a first set of multilayer Laue lenses (MLLs) having multiple layers of X-ray refractive material arranged in a first direction to diffract the redirected X-rays that are incident thereupon, and a second set of MLLs having multiple layers of X-ray refractive material arranged in a second direction to receive X-rays after diffraction by the first set of MLLs.

3. The light field X-ray optical system of claim 2, wherein the multiple layers of the first set of MLLs are separated from one another at different spacing values.

4. The light field X-ray optical system of claim 2, wherein a distance between the first set of MLLs and the second set of MLLs is in a range between 0 to 1 mm.

5. The light field X-ray optical system of claim 2, wherein one or both of the first set of MLLs or the second set of MLLs is positioned at an offset from an exact location of the intermediate image plane.

6. The light field X-ray optical system of claim 2, wherein one or both a number of layers or a spacing between the multiple layers in the first set of MLLs is different from a number of layers or a spacing between the multiple layers in the second set of MLLs.

7. The light field X-ray optical system of claim 2, wherein the first direction is substantially perpendicular to the second direction, and wherein an angle between the first direction and the second direction is in a range of 80 degrees to 100 degrees.

8. The light field X-ray optical system of claim 2, wherein thicknesses of the multiple layers of the first set and the second set of MLLs are determined based on a predetermined focal length value of the microlens array and an energy of the incoming X-rays.

9. The light field X-ray optical system of claim 2, wherein the primary optics subsection includes a third set of MLLs arranged in a third direction and a fourth set of MLLs arranged in a fourth direction, the third and fourth directions being substantially perpendicular to each other.

10. The light field X-ray optical system of claim 1, wherein the microlens array comprises an array of zone plates.

11. The light field X-ray optical system of claim 10, wherein each zone plate in the array of zone plates has a diameter in a range of 0.01 to 0.2 mm, and wherein each zone plate in the array of zone plates has a thickness in a range of 0.1 to 5 μm.

12. The light field X-ray optical system of claim 1, wherein the primary optics subsection includes a Wolter lens configured to receive the incoming X-rays at grazing incident angles.

13. The light field X-ray optical system of claim 12, wherein the Wolter lens has a diameter in a range 25 mm to 200 mm, wherein the Wolter lens has a length in a range 50 mm to 400 mm, and wherein the Wolter lens has a focal length in a range 200 mm to 1 meter.

14. The light field X-ray optical system of claim 1, wherein the primary optics subsection includes a zone plate.

15. The light field X-ray optical system of claim 1, further comprising:
a pixelated detector positioned at a focal plane of the microlens array to receive X-rays from the microlens array and to produce electrical signals or associated information in response thereto; and
a processing system coupled to the pixelated detector to receive the electrical signals or associated information and to determine a three-dimensional structure of the object.

* * * * *